(12) United States Patent
Bertin

(10) Patent No.: US 6,756,196 B2
(45) Date of Patent: Jun. 29, 2004

(54) MOLECULES OF THE CARD-RELATED PROTEIN FAMILY AND USES THEREOF

(75) Inventor: John Bertin, Watertown, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 32 days.

(21) Appl. No.: 09/841,879

(22) Filed: Apr. 24, 2001

(65) Prior Publication Data

US 2002/0142979 A1 Oct. 3, 2002

Related U.S. Application Data

(63) Continuation-in-part of application No. 09/728,721, filed on Dec. 1, 2000, which is a continuation-in-part of application No. 09/340,620, filed on Jun. 28, 1999.

(51) Int. Cl.$^7$ ................................................. C12Q 1/00
(52) U.S. Cl. ................................ 435/4; 435/6; 435/7.1
(58) Field of Search ................................ 435/4, 6, 7.1

(56) References Cited

FOREIGN PATENT DOCUMENTS

| WO | WO 98/55507 | 12/1998 |
|----|-------------|---------|
| WO | WO99/55134 | 4/1999 |
| WO | WO 99/40102 | 8/1999 |
| WO | WO 99/47669 | 9/1999 |
| WO | WO 00/06728 | 2/2000 |
| WO | WO 01/00826 A2 | 1/2001 |

OTHER PUBLICATIONS

Baker et al., "Transducers of life and death: TNF receptor superfamily and associated proteins" Oncogene 12:1–9, 1996.
Bertin et al., Human CARD4 Protein Is A Novel CED–4/Apaf–1 Cell Death Family Member . . . : J. of Biol. Chem. 274:12955–12958, 1999.
Chinnaiyan et al., "The cell–death machine" Current Biology 6:555–562, 1996.
Conway et al., "TMS1, a Novel Proapoptotic Caspase Recruitment Domain Protein, Is a Target of Methylation–induced Gene Silencing in Human Breast Cancers," Cancer Research 60:6236–6242 (2000).
Duan et al., "RAIDD is a new death adaptor molecule" Nature 385:86–89, 1997.
Epstein, F., "Nuclear factor–kB–A pivotal transcription factor in chronic inflammatory diseases" The New England J. of Medicine 336:1066–1071, 1997.
Hofman et al., "The CARD domain: a new apoptotic signalling motif" TIBS 22:155–156, 1997.
Hu et al., "Bcl–X$^L$ interacts wtih Apaf–1 and inhibits Apaf–1–dependent caspase–9 activation" Proc. Nat'l. Acad. Sci. USA 95:4386–4391, 1998.
Humke et al., "ICEBERG: A Novel Inhibitor of Interleukin–1β Generation" Cell 103:99–111, Sep. 29, 2000.

Inohara et al., "RICK, a novel protein kinase containing a caspase recruitment domain, interacts with . . . " J. of Biol. Chem. 273(20):12296–12300, 1998.
Inohara et al., "NODI, an Apaf–1–like Activator of Caspase–9 and Nuclear Factor kB" J. of Biol. Chem. 274:14560–14567, 1999.
Li et al., "Cytochrome c and dATP–dependent formation of Apaf–1/caspase–9 complex initiates and apoptotic protease cascade" Cell 91:479–489, 1997.
Marra et al., EMBL Accession No. AA620157, Sep. 12, 1996.
Masumoto et al., "ASC, a Novel 22–kDa Protein, Aggregates During Apoptosis of . . . " J. of Biol. Chem. 274(48):33835–33838, 1999.
McCarthy et al., "RIP2 is a novel NF–kB–activating and cell death–inducing kinase" J. of Biol. Chem. 273(27):16968–16975, 1998.
McConnell et al., "Activation of a Caspase–9–mediated Apoptotic Pathway to Subcellular Redistribution of the Novel Caspase Recuitment Domain Protein TMS1," Cancer Research 60:6243–6247 (2000).
Miura et al., "Induction of apoptosis in fibroblasts by IL–1β–converting enzyme, a mammalian homolog . . . " Cell 75:653–660, 1993.
Navab et al., "Pathogenesis of Atherosclerosis" American J. of Cardiology 76:18c–23c, 1995.
Reed, J., "Cytochrome c: Can't live with it–Can't live without it" Cell 91:559–562, 1997.
Srinivasula et al., "The Pyrin–Card Protein ASC Is an Activating Adaptor for Caspase–1," J. Biological Chemistry 277(24):21119–21122 (2002).
Wallach, D., "Cell death induction by TNF: a matter of self control" TIBS 22:107–109, 1997.
Yan et al., "mE10, a novel caspase recruitment domain–containing proapoptotic molecule" J. of Bio. Chem. 274(15)10287–10292, 1999.
GenBank Accession No. AA160647, Hillier et al., Dec. 1996.
GenBank Accession No. AA160649, Hillier et al., Dec. 1996.
GenBank Accession No. AA278825, Strausberg, Aug. 15, 1997.

(List continued on next page.)

Primary Examiner—Sean McGarry
(74) Attorney, Agent, or Firm—Fish & Richardson P.C.

(57) ABSTRACT

Novel CARD-5 polypeptides, proteins, and nucleic acid molecules are disclosed. In addition to CARD-5 proteins, and the invention further provides CARD-5 fusion proteins, antigenic peptides and anti-CARD-5 antibodies. The invention also provides CARD-5 nucleic acid molecules, recombinant expression vectors containing a nucleic acid molecule of the invention, host cells into which the expression vectors have been introduced and non-human transgenic animals in which a CARD-5 gene has been introduced or disrupted. Diagnostic, screening and therapeutic methods utilizing compositions of the invention are also provided.

48 Claims, 8 Drawing Sheets

OTHER PUBLICATIONS

GenBank Accession No. AA302352, Kerlavage, Apr. 18, 1997.
GenBank Accession No. AA528254, Strausberg, Aug. 5, 1997.
GenBank Accession No. AA573948, Strausberg, Sep. 12, 1997.
GenBank Accession No. AA582937, Strausberg, Sep. 26, 1997.
GenBank Accession No. AA723533, Hillier et al., Jan. 1998.
GenBank Accession No. AB023416, Masumoto et al., Dec. 1, 1999.
GenBank Accession No. AI148558, Strausberg, Oct. 28, 1998.
GenBank Accession No. AI262374, Strausberg, Nov. 13, 1998.
GenBank Accession No. AI346818, Strausberg, Feb. 2, 1998.
GenBank Accession No. AI570067, Strausberg, May 14, 1998.
GenBank Accession No. AI587178, Strausberg, May 14, 1998.
GenBank Accession No. AI821342, Strausberg, Jul. 9, 1998.
GenBank Accession No. AW192194, Strausberg, Nov. 29, 1999.
GenBank Accession No. AW196663, Strausberg, Nov. 29, 1999.
GenBank Accession No. R84288, Aug. 14, 1995.
Accession No. AB032249 (Oct. 14, 2000).
Accession No. AF184072 (Aug. 22, 2000).
Accession No. AF184073 (Aug. 22, 2000).
Accession No. AF310103 (Nov. 6, 2000)
Accession No. AF310104 (Nov. 6, 2000)
Accession No. BF302423 (Nov. 23, 2000)
EMBL Accession No. AB023416, Dec. 1, 1999.
PCT Search Report dated Sep. 30, 2002, PCT/US01/44894.

1 GTCGACCCACGCGTCCGGCAGCAGGCAGGCTGCAGCAGGCGAGCAGCAGCAAGAGTAAAAGG
  CAGCTGGGTGCGCAGGCCGTCGTCCGTCCGACGTCGTCCGCTCGTCGTCGTTCTCATTTTCC

63 TGACCGCGGCTGCCCACCCCAGAGCCATGGGGCGGGCACGAGATGCCATCCTGGACGCTCTT
   ACTGGCGCCGACGGGTGGGGTCTCGGTACCCCGCCCGTGCTCTACGGTAGGACCTGCGAGAA
   1▶ M  G  R  A  R  D  A  I  L  D  A  L

125 GAAAACTTGTCAGGGGATGAACTCAAAAAGTTCAAGATGAAGCTGCTGACAGTGCAACTGCG
    CTTTTGAACAGTCCCCTACTTGAGTTTTTCAAGTTCTACTTCGACGACTGTCACGTTGACGC
    13▶ E  N  L  S  G  D  E  L  K  K  F  K  M  K  L  L  T  V  Q  L  R

187 AGAAGGCTATGGGCGCATCCCACGCGGGGCCCTGCTGCAGATGGACGCCATAGATCTCACTG
    TCTTCCGATACCCGCGTAGGGTGCGCCCCGGGACGACGTCTACCTGCGGTATCTAGAGTGAC
    33▶ E  G  Y  G  R  I  P  R  G  A  L  L  Q  M  D  A  I  D  L  T

249 ACAAACTTGTCAGCTACTATCTGGAGTCGTATGGCTTGGAGCTCACAATGACTGTGCTTAGA
    TGTTTGAACAGTCGATGATAGACCTCAGCATACCGAACCTCGAGTGTTACTGACACGAATCT
    54▶ D  K  L  V  S  Y  Y  L  E  S  Y  G  L  E  L  T  M  T  V  L  R

311 GACATGGGCTTACAGGAGCTGGCTGAGCAGCTGCAAACGACTAAAGAAGAGTCTGGAGCTGT
    CTGTACCCGAATGTCCTCGACCGACTCGTCGACGTTTGCTGATTTCTTCTCAGACCTCGACA
    75▶ D  M  G  L  Q  E  L  A  E  Q  L  Q  T  T  K  E  E  S  G  A  V

373 GGCAGCTGCAGCCAGTGTCCCTGCTCAGAGTACAGCCAGAACAGGACACTTTGTGGACCAGC
    CCGTCGACGTCGGTCACAGGGACGAGTCTCATGTCGGTCTTGTCCTGTGAAACACCTGGTCG
    95▶ A  A  A  A  S  V  P  A  Q  S  T  A  R  T  G  H  F  V  D  Q

435 ACAGGCAAGCACTCATTGCCAGGGTCACAGAAGTGGACGGAGTGCTGGATGCTTTGCATGGC
    TGTCCGTTCGTGAGTAACGGTCCCAGTGTCTTCACCTGCCTCACGACCTACGAAACGTACCG
    116▶ H  R  Q  A  L  I  A  R  V  T  E  V  D  G  V  L  D  A  L  H  G

497 AGTGTGCTGACTGAAGGACAGTACCAGGCAGTTCGTGCAGAGACCACCAGCCAAGACAAGAT
    TCACACGACTGACTTCCTGTCATGGTCCGTCAAGCACGTCTCTGGTGGTCGGTTCTGTTCTA
    137▶ S  V  L  T  E  G  Q  Y  Q  A  V  R  A  E  T  T  S  Q  D  K  M

559 GAGGAAGCTCTTCAGCTTTGTTCCATCCTGGAACCTGACCTGCAAGGACTCCCTCCTCCAGG
    CTCCTTCGAGAAGTCGAAACAAGGTAGGACCTTGGACTGGACGTTCCTGAGGGAGGAGGTCC
    157▶ R  K  L  F  S  F  V  P  S  W  N  L  T  C  K  D  S  L  L  Q

621 CCTTGAAGGAAATACATCCCTACTTGGTGATGGACCTGGAGCAGAGCTGAGGTATCTTTTCC
    GGAACTTCCTTTATGTAGGGATGAACCACTACCTGGACCTCGTCTCGACTCCATAGAAAAGG (SEQ ID NO:3)
    178▶ A  L  K  E  I  H  P  Y  L  V  M  D  L  E  Q  S (SEQ ID NO:2)

683 AGCTACATTATCTAGCTCCTGACTTTGTATACACAATTTTTGAAAAAACAATTTGTATTTGT
    TCGATGTAATAGATCGAGGACTGAAACATATGTGTTAAAAACTTTTTTGTTAAACATAAACA

745 GTTTAAAAAAAAAAAAAAAAAAAAGGGCGGCCGC (SEQ ID NO:1)
    CAAATTTTTTTTTTTTTTTTTTTTCCCGCCGGCG

FIG. 1

```
  1 CGCGTCCGGCTGCAGCGGGGTGAGCGGCGGCAGCGGCCGGGGATCCTGGAGCCATGGGGC
    GCGCAGGCCGACGTCGCCCCACTCGCCGCCGTCGCCGGCCCCTAGGACCTCGGTACCCCG
                                                           1▶ M   G

61 GCGCGCGCGACGCCATCCTGGATGCGCTGGAGAAACCTGACCGCCGAGGAGCTCAAGAAGT
    CGCGCGCGCTGCGGTAGGACCTACGCGACCTCTTGGACTGGCGGCTCCTCGAGTTCTTCA
  3▶ R   A   R   D   A   I   L   D   A   L   E   N   L   T   A   E   E   L   K   K

121 TCAAGCTGAAGCTGCTGTCGGTGCCGCTGCGCGAGGGCTACGGGCGCATCCCGCGGGGCG
    AGTTCGACTTCGACGACAGCCACGGCGACGCGCTCCCGATGCCCGCGTAGGGCGCCCCGC
 23▶ F   K   L   K   L   L   S   V   P   L   R   E   G   Y   G   R   I   P   R   G

181 CGCTGCTGTCCATGGACGCCTTGGACCTCACCGACAAGCTGGTCAGCTTCTACCTGGAGA
    GCGACGACAGGTACCTGCGGAACCTGGAGTGGCTGTTCGACCAGTCGAAGATGGACCTCT
 43▶ A   L   L   S   M   D   A   L   D   L   T   D   K   L   V   S   F   Y   L   E

241 CCTACGGCGCCGAGCTCACCGCTAACGTGCTGCGCGACATGGGCCTGCAGGAGATGGCCG
    GGATGCCGCGGCTCGAGTGGCGATTGCACGACGCGCTGTACCCGGACGTCCTCTACCGGC
 63▶ T   Y   G   A   E   L   T   A   N   V   L   R   D   M   G   L   Q   E   M   A

301 GGCAGCTGCAGGCGGCCACGCACCAGGGCTCTGGAGCCGCGCCAGCTGGGATCCAGGCCC
    CCGTCGACGTCCGCCGGTGCGTGGTCCCGAGACCTCGGCGCGGTCGACCCTAGGTCCGGG
 83▶ G   Q   L   Q   A   A   T   H   Q   G   S   G   A   A   P   A   G   I   Q   A

361 CTCCTCAGTCGGCAGCCAAGCCAGGCCTGCACTTTATAGACCAGCACCGGGCTGCGCTTA
    GAGGAGTCAGCCGTCGGTTCGGTCCGGACGTGAAATATCTGGTCGTGGCCCGACGCGAAT
103▶ P   P   Q   S   A   A   K   P   G   L   H   F   I   D   Q   H   R   A   A   L

421 TCGCGAGGGTCACAAACGTTGAGTGGCTGCTGGATGCTCTGTACGGGAAGGTCCTGACGG
    AGCGCTCCCAGTGTTTGCAACTCACCGACGACCTACGAGACATGCCCTTCCAGGACTGCC
123▶ I   A   R   V   T   N   V   E   W   L   L   D   A   L   Y   G   K   V   L   T

481 ATGAGCAGTACCAGGCAGTGCGGGCCGAGCCCACCAACCCAAGCAAGATGCGGAAGCTCT
    TACTCGTCATGGTCCGTCACGCCCGGCTCGGGTGGTTGGGTTCGTTCTACGCCTTCGAGA
143▶ D   E   Q   Y   Q   A   V   R   A   E   P   T   N   P   S   K   M   R   K   L

541 TCAGTTTCACACCAGCCTGGAACTGGACCTGCAAGGACTTGCTCCTCCAGGCCCTAAGGG
    AGTCAAAGTGTGGTCGGACCTTGACCTGGACGTTCCTGAACGAGGAGGTCCGGGATTCCC
163▶ F   S   F   T   P   A   W   N   W   T   C   K   D   L   L   L   Q   A   L   R

601 AGTCCCAGTCCTACCTGGTGGAGGACCTGGAGCGGAGCTGAGGCTCCTTCCCAGCAACAC
    TCAGGGTCAGGATGGACCACCTCCTGGACCTCGCCTCGACTCCGAGGAAGGGTCGTTGTG (SEQ ID NO:6)
183▶ E   S   Q   S   Y   L   V   E   D   L   E   R   S (SEQ ID NO:5)

661 TCCGGTCAGCCCCTGGCAATCCCACCAAATCATCCTGAATCTGATCTTTTTATACACAAT
    AGGCCAGTCGGGGACCGTTAGGGTGGTTTAGTAGGACTTAGACTAGAAAAATATGTGTTA

721 ATACGAAAAGCCAGCTTGAA (SEQ ID NO:4)         FIG. 3
    TATGCTTTTCGGTCGAACTT
```

ALIGN calculates a global alignment of two sequences
version 2.0uPlease cite: Myers and Miller, CABIOS (1989)
> hCARD5-DNA                                                           740 aa vs.
> mCARD5-DNA                                                           763 aa
scoring matrix: pam120.mat, gap penalties: -12/-4
68.2% identity;   Global alignment score: 2377

```
                   10        20        30
inputs   C---GCGTCCGGCTGCAG-CGGGGTG-----AGCG-GCGGCAGC-------------GGC
         :   ::::::::::.:::: :..:: ::      .:::  ::..::::::           :.:
         CCACGCGTCCGGCAGCAGGCAGGCTGCAGCAGGCGAGCAGCAGCAAGAGTAAAAGGTGAC
            10        20        30        40        50        60

40        50        60        70        80        90
inputs   CGGGGAT------CCTGGAGCCATGGGGCGCGCGCGCGACGCCATCCTGGATGCGCTGGA
         ::  ::  :         ::  .:::::::::::::  ::.:::  ::  :::::::::::  ::  ::  ::
         CGCGGCTGCCCACCCCAGAGCCATGGGGCGGGCACGAGATGCCATCCTGGACGCTCTTGA
            70        80        90       100       110       120

100       110       120       130       140       150
inputs   GAACCTGACCGCCGAGGAGCTCAAGAAGTTCAAGCTGAAGCTGCTGTCGGTGCCGCTGCG
         .:::  ::.:  :  :: ::.::::::::.:::::::: :::::::::::::.:.::::  .::::: 
         AAACTTGTCAGGGGATGAACTCAAAAAGTTCAAGATGAAGCTGCTGACAGTGCAACTGCG
           130       140       150       160       170       180

160       170       180       190       200       210
inputs   CGAGGGCTACGGGCGCATCCCGCGGGGCGCGCTGCTGTCCATGGACGCCTTGGACCTCAC
         ::.:::::  :::::::::  ::  ::  ::::::.      .::::::::::.::  ::::: 
         AGAAGGCTATGGGCGCATCCCACGCGGGGCCCTGCTGCAGATGGACGCCATAGATCTCAC
           190       200       210       220       230       240

220       230       240       250       260       270
inputs   CGACAAGCTGGTCAGCTTCTACCTGGAGACCTACGGCGCCGAGCTCACCGCTAAC-GTGC
         :::::.::  :::::::::.:::  ::::::::::.: ::  :::          :::::::::  .  :.:: ::::
         TGACAAACTTGTCAGCTACTATCTGGAGTCGTATGGCTTGGAGCTCAC-AATGACTGTGC
           250        260       270       280       290

280       290       300       310       320       330
inputs   TGCGCGACATGGGCCTGCAGGAGATGGCCGGGCAGCTGCAGGCGGCCACGCACCAGGGCT
         :   :  :::::::::::  :.:::::: ::::    :.:::::::::::..:::.:  :  .  :  ::.. :
         TTAGAGACATGGGCTTACAGGAGCTGGCTGAGCAGCTGCAAACGACTAAAGA--AGAG-T
             300       310       320       330       340       350

340       350       360       370       380       390
inputs   CTGGAGCCGCGCCAGCTGGGATCCAGGCCCCTCCTCAGTCGGCAGCCAAGCCAGGCCTGC
         :::::::: : : :::::::  .. : . :  ::::::.   .::::::::.. ::::       ..:
         CTGGAGCTGTGGCAGCTGCAGCCAGTGTCCCTGCTCAGAGTACAGCCAGAACAGG---AC
           360       370       380       390       400       410

```
inputs ACTTTATAGACCAGCACCGGGCTGCGCTTATCGCGAGGGTCACAAACGTTGAGTGGCTGC
       ::::: : ::::::::::: ::  ..::.:: :: :: :::::::::: :: ::  :. :::
       ACTTTGTGGACCAGCACAGGCAAGCACTCATTGCCAGGGTCACAGAAGTGGACGGAGTGC
          420       430       440       450       460       470

460       470       480       490       500       510
inputs TGGATGCTCTGTACGGGAAGGTCCTGACGGATGAGCAGTACCAGGCAGTGCGGGCCGAGC
       :::::::: :: : :: :. :: ::::: :::..:::::::::::::: :: :: :::
       TGGATGCTTTGCATGGCAGTGTGCTGACTGAAGGACAGTACCAGGCAGTTCGTGCAGAGA
          480       490       500       510       520       530

520       530       540       550       560       570
inputs CCACCAACCCAAGCAAGATGCGGAAGCTCTTCAGTTTCACACCAGCCTGGAACTGGACCT
       ::::::.::  :...:::::: ::::::::::: :: . .::: :::::::  :::::
       CCACCAGCCAAGACAAGATGAGGAAGCTCTTCAGCTTTGTTCCATCCTGGAACCTGACCT
          540       550       560       570       580       590

580       590       600       610       620       630
inputs GCAAGGACTTGCTCCTCCAGGCCCTAAGGGAGTCCCAGTCCTACCTGGTGGAGGACCTGG
       ::::::::::   :::::::::::: :.:.::::..  ::  ::::: :::::..:::::::::
       GCAAGGACTCCCTCCTCCAGGCCTTGAAGGAAATACATCCCTACTTGGTGATGGACCTGG
          600       610       620       630       640       650

640       650       660       670       680
inputs AGCGGAGCTGAGGC-TCCTTCCCAGCAACACTCCGGTC-AGCCCCTGGCAAT-CCCAC-C
       :::..:::::::::  ::  :: :::::.::: :    .:: ::: :::::..:   :: :
       AGCAGAGCTGAGGTATCTTTTCCAGCTACATT---ATCTAGCTCCTGACTTTGTATACAC
          660       670       680       690       700       710

690       700       710       720       730       740
inputs AAATCATCCTGAATCTGATCTTTTTATACACAATATACGAAAAGCCAGCTTGAA (SEQ ID NO:4)
       ::.: .:  ..::.:....: : :.:.:. . ...:.: :::::. :. .....
       AATTTTTGAAAAAACAATT-TGTATTTGTGTTTAAAAAAAAAAAAAAAAAAAGG (SEQ ID NO:1)
          720       730       740       750       760
```

FIG. 5B

```
ALIGN calculates a global alignment of two sequences
 version 2.0uPlease cite: Myers and Miller, CABIOS (1989)
> hCARD5-protein                                    195 aa vs.
> mCARD5-protein                                    193 aa
scoring matrix: pam120.mat, gap penalties: -12/-4
71.8% identity;    Global alignment score: 712

10        20        30        40        50        60
inputs  MGRARDAILDALENLTAEELKKFKLKLLSVPLREGYGRIPRGALLSMDALDLTDKLVSFY
        ::::::::::::::::...:::::::.:::.:.:::::::::::::: :::.:::::::..:
        MGRARDAILDALENLSGDELKKFKMKLLTVQLREGYGRIPRGALLQMDAIDLTDKLVSYY
                10        20        30        40        50        60

70        80        90       100       110       120
inputs  LETYGAELTANVLRDMGLQEMAGQLQAATHQGSGAAPAGIQAPPQSAAKPGLHFIDQHRA
        ::.:: :::  .:::::::::: :::. : . ::::... ..:.::. :  :: .::::
        LESYGLELTMTVLRDMGLQELAEQLQT-TKEESGAVAAAASVPAQSTARTG-HFVDQHRQ
                70        80        90       100       110

130       140       150       160       170       180
inputs  ALIARVTNVEWLLDALYGKVLTDEQYQAVRAEPTNPSKMRKLFSFTPAWNWTCKDLLLQA
        :::::::.:.  .::::  :  :::. :::::::::: :...::::::::::.:.:: :::: ::::
        ALIARVTEVDGVLDALHGSVLTEGQYQAVRAETTSQDKMRKLFSFVPSWNLTCKDSLLQA
               120       130       140       150       160       170

190
inputs  LRESQSYLVEDLERS  (SEQ ID NO:5)
        :.: ..::: ::::.:
        LKEIHPYLVMDLEQS  (SEQ ID NO:2)              FIG. 6
               180       190
```

FIG. 8

MOLECULES OF THE CARD-RELATED PROTEIN FAMILY AND USES THEREOF

CROSS REFERENCE TO RELATED APPLICATIONS

This application is a continuation-in-part of U.S. application Ser. No. 09/728,721, filed Dec. 1, 2000, which is a continuation-in-part of U.S. application Ser. No. 09/340,620, filed Jun. 28, 1999. The contents of each of these applications are incorporated herein by reference.

BACKGROUND OF THE INVENTION

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA. The various signals that trigger apoptosis are thought to bring about these events by converging on a common cell death pathway that is regulated by the expression of genes that are highly conserved from worms, such as C. elegans, to humans. In fact, invertebrate model systems have been invaluable tools in identifying and characterizing the genes that control apoptosis. Through the study of invertebrates and more evolved animals, numerous genes that are associated with cell death have been identified, but the way in which their products interact to execute the apoptotic program is poorly understood.

Caspases, a class of proteins central to the apoptotic program, are responsible for the degradation of cellular proteins that leads to the morphological changes seen in cells undergoing apoptosis. Caspases (cysteinyl aspartate-specific proteinases) are cysteine proteases having specificity for aspartate at the substrate cleavage site. Generally, caspases are classified as either initiator caspases or effector caspases, both of which are zymogens that are activated by proteolysis that generates an active species. An effector caspase is activated by an initiator caspase which cleaves the effector caspase. Initiator caspases are activated by an autoproteolytic mechanism that is often dependent upon oligomerization directed by association of the caspase with an adapter molecule.

Many caspases and proteins that interact with caspases possess domains of about 60 amino acids called a caspase recruitment domain (CARD). Hofmann et al. (TIBS 22:155, 1997) and others have postulated that certain apoptotic proteins bind to each other via their CARDs and that different subtypes of CARDs may confer binding specificity, regulating the activity of various caspases, for example. The functional significance of CARDs have been repeatedly demonstrated. For example, Duan et al. (Nature 385:86, 1997) showed that deleting the CARD at the N-terminus of RAIDD abolished the ability of RAIDD to bind to caspases.

Caspase-1 is an example of an initiator caspase. Caspase-1 was first discovered as the protease responsible for the conversion of the inactive precursor of IL-1 to the mature proinflammatory cytokine (caspase-1 was originally termed interleukin-1 converting enzyme, ICE). Caspase-1 also processes the inactive precursor of the cytokine IL-18 into an active form. Caspase-1 is synthesized as a single chain zymogen consisting of an N-terminal CARD containing prodomain and a large (p20) and small (p 10) catalytic domain. Caspase-1 is thought to oligomerize upon the receipt of a proinflammatory signal and autoprocess to generate an active heterodimeric protease consisting of the p20 and p10 subunits.

RIP2 (CARDIAK/RICK) binds caspase-1 via an interaction between the CARD domain of RIP2 and the CARD domain of caspase-1. This interaction results in the processing and activation of caspase-1. Thus, RIP2 is thought to be an upstream activator adaptor of caspase-1. Conversely, the activation of caspase-1 and subsequent generation of IL-1 P is regulated by a CARD domain-containing decoy molecule termed ICEBERG. This decoy attenuates inflammation by binding to the CARD domain of caspase-1 and inhibiting or displacing the upstream activator RIP2. ICEBERG is induced by proinflammatory stimuli and thus appears to be part of a negative feedback loop that shuts off IL-1β generation and thus dampens the inflammatory response (Humke et al., Cell 103:99, 2000).

In addition to its role in inflammation via IL-1β processing, caspase-1 also appears to participate in cell death pathways. For example, overexpression of caspase-1 in Rat-1 fibroblasts induces apoptosis that can be suppressed by overexpression of antiapoptotic genes such as Bcl-2 (Miura et al., Cell 75:653, 1993).

Caspase-9 activation may precede the activation of all other cell death-related caspases in the mitochondrial pathways of apoptosis (Slee et al., J. Cell Biol. 144:281–292, 1999). Inactive procaspase-9 is activated by interaction with a complex which includes Apaf-1, a CARD-containing protein, and other factors (Li et al., Cell 91:479, 1997; Srinivasula et al., Mol. Cell 1:949–959, 1998). Recognition of procaspase-9 by Apaf-1 occurs primarily through the interaction of the CARD of Apaf-1 with the prodomain of caspase-9. The CARD of Apaf-1 shares about 20% sequence identity with the prodomain of procaspase-9. The prodomain of caspase-9 is a member of the CARD family of apoptotic signaling motifs (Hofmann and Bucher, Trends in Biochem. Sci. 22:155–156, 1997). A similar domain is present in caspase activating proteins CED-4 and RAIDD/CRADD as well as in initiator caspases CED-3 and caspase-2/ICH-1 (Duan and Dixit, Nature 385:86–89, 1997; Ahmad et al., Cancer Res. 57:615–619, 1997; Alnemri et al., Cell 87:171, 1996). Apaf-1 can bind several other caspases, e.g., caspase-4 and caspase-8 (Inohara et al., J. Biol. Chem. 273:12296–12300, 1998).

Nuclear factor-κB (NF-κB) is a transcription factor expressed in many cell types and which activates homologous or heterologous genes that have κB sites in their promoters. Molecules that regulate NF-κB activation play a critical role in both apoptosis and inflammation. Quiescent NF-κB resides in the cytoplasm as a heterodimer of proteins referred to as p50 and p65 and is complexed with the regulatory protein IκB. NF-κB binding to IκB causes NF-κB to remain in the cytoplasm. At least two dozen stimuli that activate NF-κB are known (New England Journal of Medicine 336:1066, 1997) and they include cytokines, protein kinase C activators, oxidants, viruses, and immune system stimuli. NF-κB activating stimuli activate specific IκB kinases that phosphorylate IκB leading to its degradation. Once liberated from IκB, NF-κB translocates to the nucleus and activates genes with κB sites in their promoters. The proinflammatory cytokines TNF-α and IL-1 induce NF-κB activation by binding their cell-surface receptors and activating the NF-κB-inducing kinase, NIK, and NF-κB. NIK phosphorylates the IκB kinases α and β which phosphorylate IκB, leading to its degradation.

NF-κB and the NF-κB pathway has been implicated in mediating chronic inflammation in inflammatory diseases such as asthma, ulcerative colitis, rheumatoid arthritis (Epstein, New England Journal of Medicine 336:1066, 1997) and inhibiting NF-κB or NF-κB pathways may be an effective way of treating these diseases. NF-κB and the NF-κB pathway has also been implicated in atherosclerosis (Navab et al., American Journal of Cardiology 76:18C, 1995), especially in mediating fatty streak formation, and inhibiting NF-κB or NF-κB pathways may be an effective therapy for atherosclerosis. Among the genes activated by NF-κB are cIAP-1, cIAP-2, TRAF1, and TRAF2, all of which have been shown to protect cells from TNF-α induced cell death (Wang et al., Science 281:1680–83, 1998). CLAP, a protein which includes a CARD, activates the Apaf-1-caspase-9 pathway and activates NF-κB by acting upstream of NIK and IκB kinase (Srinivasula et al., supra).

Bcl-2 family proteins are important regulators of pathways involved in apoptosis and can act to inhibit or promote cell death. Expression of certain anti-apoptotic Bcl-2 family members is commonly altered in cancerous cells, suppressing programmed cell death and extending tumor growth. Among the anti-apoptotic Bcl-2 family members thus far identified are Boo, Bcl-2, Bcl-$x_L$, Bcl-w, NR-13, A1, and Mcl-2. Pro-apoptotic Bcl-2 family members include Bax, Bak, Bad, Bik, Bid, Hrk, Bim, and Bok/Mtd. Significantly, the anti-apoptotic Bcl-2 family member, Bcl-$x_L$, has been shown to interact with Apaf-1 and block Apaf-1-dependent caspase-9 activation (Hu et al., Proc. Nat'l. Acad. Sci. 95:4386–4391, 1998). Boo, another anti-apoptotic Bcl-2 family member, interacts with Apaf-1 and caspase-9. Bak and Bik, pro-apoptotic Bcl-2 family members, can disrupt the association of Boo with Apaf-1 (Song et al., EMBO J. 18:167–178, 1999). Boo is thought to be involved in the control of ovarian atresia and sperm maturation. Diva, another member of the Bcl-2 family, inhibits binding of Bcl-$x_L$ to Apf-1, preventing Bcl-$x_L$ from binding to Apaf-1.

Neurotrophins (e.g., NGF), which are best known as neuronal survival factors, can mediate apoptosis via the p75 neurotrophin receptor ($p75^{NTR}$). It is thought that $p75^{NTR}$ activation can lead to NF-κB activation (Carter et al., Science 272:542–545, 1996). It has been proposed that $p75^{NTR}$-mediated cell death acts to ensure rapid cell death when a neuron is unable to obtain sufficient neurotropins. This mechanism could, for example, cause the elimination of neurons that reach an inappropriate target or that reach an appropriate target at an inappropriate time (Miller and Kaplan, Cell Death and Diff. 5:343–345, 1998).

SUMMARY OF THE INVENTION

The present invention is based, at least in part, on the discovery of genes encoding CARD-5. Full-length cDNAs encoding murine and human CARD-5 are presented.

CARD-5 is an intracellular protein that is predicted to be involved in regulating caspase activation. CARD-5 is found to activate the NF-κB pathway and to bind to the CARD domains of caspase-1, CARD-7, and CARD-5 itself.

The 777 nucleotide murine CARD-5 cDNA described below (SEQ ID NO:1) has a 579 nucleotide open reading frame (nucleotides 89 to 667 of SEQ ID NO: 1; SEQ ID NO:3) which encodes a 193 amino acid protein (SEQ ID NO:2). Murine CARD-5 contains a CARD domain which extends from amino acid 110 to amino acid 193 of SEQ ID NO:2 (SEQ ID NO:7).

The 740 nucleotide human CARD-5 cDNA described below (SEQ ID NO:4) has a 585 nucleotide open reading frame (nucleotides 54 to 638 of SEQ ID NO:4; SEQ ID NO:6) which encodes a 195 amino acid protein (SEQ ID NO:5). Human CARD-5 contains a CARD domain which extends from amino acid 111 to amino acid 195 of SEQ ID NO:5 (SEQ ID NO:8).

Like other proteins containing a CARD domain CARD-5 participates in the network of interactions that lead to caspase activity. Human CARD-5 likely plays functional roles in caspase activation similar to that of FADD. CARD-5 through its CARD and pyrin domains may interact with other proteins having a CARD domain and/or a pyrin domain. For example, CARD-5 may serve as bridge to link a CARD domain-containing protein and/or a pyrin domain containing protein thus directly or indirectly activating signaling pathways, e.g., cell signaling pathways. CARD-5 may bind to and activate a CARD-containing caspase via a CARD—CARD interaction, leading to apoptotic death of the cell and/or cytokine processing that leads to inflammation. CARD-5 molecules are useful as modulating agents in regulating a variety of cellular processes including cell growth and cell death. In one aspect, this invention provides isolated nucleic acid molecules encoding CARD-5 proteins or biologically active portions thereof, as well as nucleic acid fragments suitable as primers or hybridization probes for the detection of CARD-5 encoding nucleic acids.

The invention encompasses methods of diagnosing and treating patients who are suffering from a disorder associated with an abnormal level or rate (undesirably high or undesirably low) of apoptotic cell death, abnormal activity of the Fas/APO-1 receptor complex, abnormal activity of the TNF receptor complex, abnormal inflammatory response, or abnormal activity of a caspase by administering a compound that modulates the expression of CARD-5 (at the DNA, mRNA or protein level, e.g., by altering mRNA splicing) or by altering the activity of CARD-5. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. Compounds that modulate the expression or activity of CARD-5 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat viral infections (such as those caused by herpesviruses, poxyiruses, and adenoviruses). Failure to remove autoimmune cells that arise during development or that develop as a result of somatic mutation during an immune response can result in autoimmune disease. Thus, autoimmune disorders can be caused by undesirably low levels of apoptosis. Accordingly, modulators of CARD-5 or activity or expression can be used to treat autoimmune disorders (e.g., systemic lupus erythematosis, immune-mediated glomerulonephritis, and arthritis).

Many diseases are associated with an undesirably high rate of apoptosis. Modulators of CARD-5 expression or activity can be used to treat or diagnose such disorders. For example, populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis. A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Proteins containing a CARD domain are thought to be involved in various inflammatory disorders. For example, the CARD domain-containing protein caspase-1 promotes inflammation by converting certain proinflammatory cytokines from an inactive to an active form. Accordingly CARD-5 polypeptides, nucleic acids and modulators of CARD-5 expression or activity can be used to treat immune disorders. Such immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

In addition to the aforementioned disorders CARD-5 polypeptides, nucleic acids, and modulators of CARD-5 expression or activity can be used to treat disorders of cell signaling and disorders of tissues in which CARD-5 is expressed.

The invention features a nucleic acid molecule which is at least 45% (or 55%, 65%, 75%, 85%, 95%, or 98%) identical to the nucleotide sequence shown in SEQ ID NO:4, SEQ ID NO:6, SEQ ID NO:1, SEQ ID NO:3, the nucleotide sequence of the cDNA insert of the plasmid deposited with the ATCC as Accession Number PTA-212 ("the cDNA of ATCC PTA-212"), the nucleotide sequence of the cDNA insert of the plasmid deposited with the ATCC as Accession Number PTA-213 (the "cDNA of ATCC PTA-213 "), or a complement thereof.

The invention also features a nucleic acid molecule which includes a fragment of at least 150 (350, 400, 450, 500, 550, 600, 650, 700, and 761) nucleotides of the nucleotide sequence shown in SEQ ID NO:1, SEQ ID NO:3, or the nucleotide sequence of the cDNA of ATCC PTA-212, or a complement thereof.

The invention also features a nucleic acid molecule which includes a fragment of at least 150 (350, 400, 450, 500, 550, 600, 650, 700, and 740) nucleotides of the nucleotide sequence shown in SEQ ID NO:4, SEQ ID NO:6, the cDNA of ATCC PTA-213, or a complement thereof.

The invention features a nucleic acid molecule which includes a nucleotide sequence encoding a protein having an amino acid sequence that is at least 45% (or 55%, 65%, 75%, 85%, 95%, or 98%) identical to the amino acid sequence of SEQ ID NO:5, SEQ ID NO:2, the amino acid sequence encoded by the cDNA of ATCC PTA-212, or the amino acid sequence encoded by the cDNA of ATCC PTA-213.

In another embodiment, a human CARD-5 nucleic acid molecule has the nucleotide sequence shown in SEQ ID NO:4, SEQ ID NO:6 or the nucleotide sequence of the cDNA of ATCC PTA-213. In another embodiment, a murine CARD-5 nucleic acid molecule has the nucleotide sequence shown in SEQ ID NO:1 or SEQ ID NO:3.

Also within the invention is a nucleic acid molecule which encodes a fragment of a polypeptide having the amino acid sequence of SEQ ID NO:5, SEQ ID NO:2, the fragment including at least 15 (25, 30, 50, 100, 150, 300, 400 or 540, 600, 700, 800, 900) contiguous amino acids of SEQ ID NO:5, SEQ ID NO:2, the polypeptide encoded by the cDNA of ATCC Accession Number PTA-212, or the polypeptide encoded by the cDNA of ATCC Accession Number PTA-213.

The invention includes a nucleic acid molecule which encodes a naturally occurring allelic variant of a polypeptide comprising the amino acid sequence of SEQ ID NO:5, SEQ ID NO:2, or an amino acid sequence encoded by the cDNA of ATCC Accession Number PTA-212, or PTA-213, wherein the nucleic acid molecule hybridizes to a nucleic acid molecule consisting of SEQ ID NO:4, SEQ ID NO:6, SEQ ID NO:1, SEQ ID NO:3, the cDNA of ATCC PTA-212, or the cDNA of PTA-213 under stringent conditions.

Also within the invention are: an isolated CARD-5 protein having an amino acid sequence that is at least about 65%, preferably 75%, 85%, 95%, or 98% identical to the amino acid sequence of SEQ ID NO:5 and an isolated CARD-5 protein comprising an amino acid sequence that is at least about 90%, 95%, or 98% identical to SEQ ID NO:8 (CARD domain).

Also within the invention are an isolated CARD-5 protein having an amino acid sequence that is at least about 65%, preferably 75%, 85%, 95%, or 98% identical to the amino acid sequence of SEQ ID NO:2 and an isolated CARD-5 protein comprising an amino acid sequence that is at least about 90%, 95%, or 98% identical to SEQ ID NO:7 (CARD domain).

Also within the invention are an isolated CARD-5 protein which is encoded by a nucleic acid molecule having a nucleotide sequence that is at least about 65%, preferably 75%, 85%, or 95% identical to SEQ ID NO:4 or the cDNA of ATCC PTA-213; an isolated CARD-5 protein which is encoded by a nucleic acid molecule having a nucleotide sequence at least about 90% preferably 95%, or 98% identical to the CARD encoding portion of SEQ ID NO:4 (e.g., about nucleotides 383 to 596 of SEQ ID NO:4); and an isolated CARD-5 protein which is encoded by a nucleic acid molecule having a nucleotide sequence which hybridizes under stringent hybridization conditions to a nucleic acid molecule having the nucleotide sequence of SEQ ID NO:4 or the non-coding strand of the cDNA of ATCC PTA-213.

Also within the invention are an isolated CARD-5 protein which is encoded by a nucleic acid molecule having a nucleotide sequence that is at least about 65%, preferably 75%, 85%, or 95% identical to SEQ ID NO:1; an isolated CARD-5 protein which is encoded by a nucleic acid molecule having a nucleotide sequence at least about 90% preferably 95%, or 98% identical to the CARD encoding portion of SEQ ID NO:1 (e.g., about nucleotides 416 to 625 of SEQ ID NO:1); and an isolated CARD-5 protein which is encoded by a nucleic acid molecule having a nucleotide sequence which hybridizes under stringent hybridization conditions to a nucleic acid molecule having the nucleotide sequence of SEQ ID NO:1.

Another embodiment of the invention features CARD-5 nucleic acid molecules which specifically detect CARD-5 nucleic acid molecules, relative to nucleic acid molecules encoding other members of the CARD superfamily. For example, in another embodiment, a CARD-5 nucleic acid molecule hybridizes under stringent conditions to a nucleic acid molecule comprising the nucleotide sequence of SEQ ID NO:4, SEQ ID NO:6, or the cDNA of ATCC PTA-213, or a complement thereof. In another embodiment, the CARD-5 nucleic acid molecule is at least 300 (350, 400, 450, 500, 550, 585, 600, 650, 700, or 740) nucleotides in length and hybridizes under stringent conditions to a nucleic acid molecule comprising the nucleotide sequence shown in SEQ ID NO:4, SEQ ID NO:6, the cDNA of ATCC PTA-213, or a complement thereof. In another embodiment, an isolated CARD-5 nucleic acid molecule comprises nucleotides 383 to 596 of SEQ ID NO:4, encoding the CARD of CARD-5. In yet another embodiment, the invention provides an isolated nucleic acid molecule which is antisense to the coding strand of a CARD-5 nucleic acid.

Another aspect of the invention provides a vector, e.g., a recombinant expression vector, comprising a CARD-5 nucleic acid molecule of the invention. In another embodiment the invention provides a host cell containing such a vector. The invention also provides a method for producing CARD-5 protein by culturing, in a suitable medium, a host cell of the invention containing a recombinant expression vector such that a CARD-5 protein is produced.

Another aspect of this invention features isolated or recombinant CARD-5 proteins and polypeptides. Preferred CARD-5 proteins and polypeptides possess at least one biological activity possessed by naturally occurring human CARD-5 e.g. (1) the ability to form protein:protein interactions with proteins in the apoptotic signaling pathway; (2) the ability to form CARD—CARD interactions with proteins in the apoptotic signaling pathway, e.g., caspase-1, CARD-12 or CARD-7; (3) the ability to bind a CARD-5 ligand; and (4) the ability to bind to an intracellular target. Other activities include: (1) modulation of cellular proliferation; (2) modulation of cellular differentiation; (3) modulation of cellular death; (4) modulation of the NF-κB pathway; (5) modulation of proinflammatory cytokine activation; and (6) modulation of inflammation.

The CARD-5 proteins of the present invention, or biologically active portions thereof, can be operatively linked to a non-CARD-5 polypeptide (e.g., heterologous amino acid sequences) to form CARD-5 fusion proteins, respectively. The invention further features antibodies that specifically bind CARD-5 proteins, such as monoclonal or polyclonal antibodies. In addition, the CARD-5 protein or biologically active portions thereof can be incorporated into pharmaceutical compositions, which optionally include pharmaceutically acceptable carriers.

Preferred CARD-5 polypeptides includes at least 15, 25, 50, 60, 70, 80, 90, 100, 125, 150, or 190 contiguous amino acids of SEQ ID NO:2 or SEQ ID NO:5. Preferred polypeptides comprise at least one domain present in CARD-5 (e.g., a CARD domain or a pyrin domain).

In another aspect, the present invention provides a method for detecting the presence of CARD-5 activity or expression in a biological sample by contacting the biological sample with an agent capable of detecting an indicator of CARD-5 activity such that the presence of CARD-5 activity is detected in the biological sample.

In another aspect, the invention provides a method for modulating CARD-5 activity comprising contacting a cell with an agent that modulates (inhibits or stimulates) CARD-5 activity or expression such that CARD-5 activity or expression in the cell is modulated. In one embodiment, the agent is an antibody that specifically binds to CARD-5 protein. In other embodiments, the compound is one which interferes with the binding of the CARD domain of CARD-5 to another CARD-domain. In another embodiment, the agent modulates expression of CARD-5, by modulating transcription of a CARD-5 gene, splicing of a CARD-5 mRNA, or translation of a CARD-5 mRNA. In yet another embodiment, the agent is a nucleic acid molecule having a nucleotide sequence that is antisense to the coding strand of the CARD-5 mRNA or the CARD-5 gene.

In one embodiment, the methods of the present invention are used to treat a subject having a disorder characterized by aberrant CARD-5 protein or nucleic acid expression or activity or related to CARD-5 expression or activity by administering an agent which is a CARD-5 modulator to the subject. In one embodiment, the CARD-5 modulator is a CARD-5 protein. In another embodiment the CARD-5 modulator is a CARD-5 nucleic acid molecule. In other embodiments, the CARD-5 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a CARD-5 protein; (ii) mis-regulation of a gene encoding a CARD-5 protein; (iii) aberrant RNA splicing; and (iv) aberrant post-translational modification of a CARD-5 protein, wherein a wild-type form of the gene encodes a protein with a CARD-5 activity.

In another aspect, the invention provides a method for identifying a compound that binds to or modulates the activity of a CARD-5 protein. In general, such methods entail measuring a biological activity of a CARD-5 protein in the presence and absence of a test compound and identifying those compounds that alter the activity of the CARD-5 protein.

The invention also features assays for identifying compounds that reduce the interaction of CARD-5 with a CARD-5 ligand, e.g., caspase-1, CARD-7, CARD-12, or CARD-5. Isolated CARD domains of CARD-5, caspase-1, CARD-12 and/or CARD-7 can be used in these assays. The assays include measuring the binding of a CARD domain containing polypeptide to a polypeptide comprising the CARD domain of CARD-5 in the presence and absence of a test compound. A test compound is identified as a compound that reduces the binding of CARD-5 with a CARD-5 ligand if the binding of the polypeptides to each other is less in the presence of the test compound than in the absence of the compound. Additional compounds can be identified by measuring the binding of a polypeptide comprising the pyrin domain of CARD-5 to a polypeptide comprising a pyrin domain (e.g., NBS-1 or Pyrin-1).

The invention also features a method for identifying compounds that alter CARD-5-mediated apoptosis. The methods entail measuring apoptosis of cells that express a polypeptide comprising the pyrin domain of CARD-5 and cells that do not express (or express at a lower level) a polypeptide comprising the pyrin domain of CARD-5 in the presence and absence of a test compound. Test compounds that reduce the apoptosis of cells expressing the pyrin domain of CARD-5 relative to cells that do not express the pyrin domain of CARD-5 are candidate selective inhibitors of CARD-5 mediated apoptosis.

Reduction of CARD-5 activity or expression may play a role in breast cancer or other cancer. Accordingly, compounds that increase the activity or expression of CARD-5 may be useful for treatment of breast cancer or other cancers.

The invention also features methods for identifying a compound that modulates the expression of CARD-5 by measuring the expression of CARD-5 in the presence and absence of a compound.

Other features and advantages of the invention will be apparent from the following detailed description and claims.

BRIEF DESCRIPTION OF THE DRAWINGS

FIG. 1 depicts the nucleotide sequence of a murine CARD-5 cDNA (SEQ ID NO:1). The open reading frame of this cDNA extends from nucleotide 89 to nucleotide 667 of SEQ ID NO:1 (SEQ ID NO:3) and encodes a 193 amino acid protein (SEQ ID NO:2). The complimentary strand is also depicted (SEQ ID NO: 18).

FIG. 3 depicts the nucleotide sequence of a human CARD-5 cDNA (SEQ ID NO:4). The open reading frame of this cDNA extends from nucleotide 54 to nucleotide 638 of SEQ ID NO:4 (SEQ ID NO:6) and encodes a 195 amino acid protein SEQ ID NO:5). The complimentary strand is also depicted (SEQ ID NO: 19).

FIG. 5 depicts an alignment of the cDNA sequences of murine CARD-5 (nucleotides 7 to 769 of SEQ ID NO:1— bottom) and human CARD-5 (SEQ ID NO:4—top). This alignment was created using ALIGN (version 2.0; PAM120 scoring matrix; −12/−4 gap penalty). In this alignment the sequences are 68.2% identical.

FIG. 6 depicts an alignment of the amino acid sequences of murine CARD-5 (SEQ ID NO:2) and human CARD-5 (SEQ ID NO:5). This alignment was created using ALIGN (version 2.0; PAM120 scoring matrix; −12/−4 gap penalty). In this alignment the sequences are 71.8% identical.

FIG. 8 depicts an alignment of the CARD domains of human CARD-3 (SEQ ID NO:10), human CARD-4 (SEQ ID NO:11), human CARD-5 (SEQ ID NO:8), murine CARD-5 (SEQ ID NO:7), human CARD-6 (SEQ ID NO:13), and rat CARD-6 (SEQ ID NO:14). This alignment was created using the Clustal method with PAM250 residue weight table. A consensus sequence is also depicted (SEQ ID NO: 12).

DETAILED DESCRIPTION OF THE INVENTION

The present invention is based, in part, on the discovery of cDNA molecules encoding murine CARD-5 and human CARD-5 proteins.

TABLE 1

Summary of CARD-5 Sequence Information.

| Gene | cDNA | Protein | ORF | Figure | Accession Number |
|---|---|---|---|---|---|
| human CARD-5 | SEQ ID NO: 4 | SEQ ID NO: 5 | SEQ ID NO: 6 | FIG. 3 | PTA-213 |
| murine CARD-5 | SEQ ID NO: 1 | SEQ ID NO: 2 | SEQ ID NO: 3 | FIG. 1 | PTA-212 |

A nucleotide sequence encoding a murine CARD-5 protein is shown in FIG. 1 (SEQ ID NO:1; SEQ ID NO:3 includes the open reading frame only). A predicted amino acid sequence of murine CARD-5 protein is also shown in FIG. 1 (SEQ ID NO:2).

A nucleotide sequence encoding a human CARD-5 protein is shown in FIG. 3 (SEQ ID NO:4; SEQ ID NO:6 includes the open reading frame only). A predicted amino acid sequence of human CARD-5 protein is also shown in FIG. 3 (SEQ ID NO:5).

The human CARD-5 cDNA of FIG. 3 (SEQ ID NO:4), which is approximately 740 nucleotides long including untranslated regions, encodes a protein having a molecular weight of approximately 21.6 kD.

A plasmid containing a cDNA encoding human CARD-5 (EpHC5) was deposited with the American Type Culture Collection (ATCC), Manasass, Va. on Jun. 11, 1999, and assigned Accession Number PTA-213. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The murine CARD-5 cDNA of FIG. 1 (SEQ ID NO:1), which is approximately 778 nucleotides long, including untranslated regions, encodes a protein having a molecular weight of approximately 21.5 kD.

A plasmid containing a cDNA encoding murine CARD-5 (EpMC5) was deposited with the American Type Culture Collection (ATCC), Manassas, Va. on Jun. 11, 1999, and assigned Accession Number PTA-212. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Figure 7:
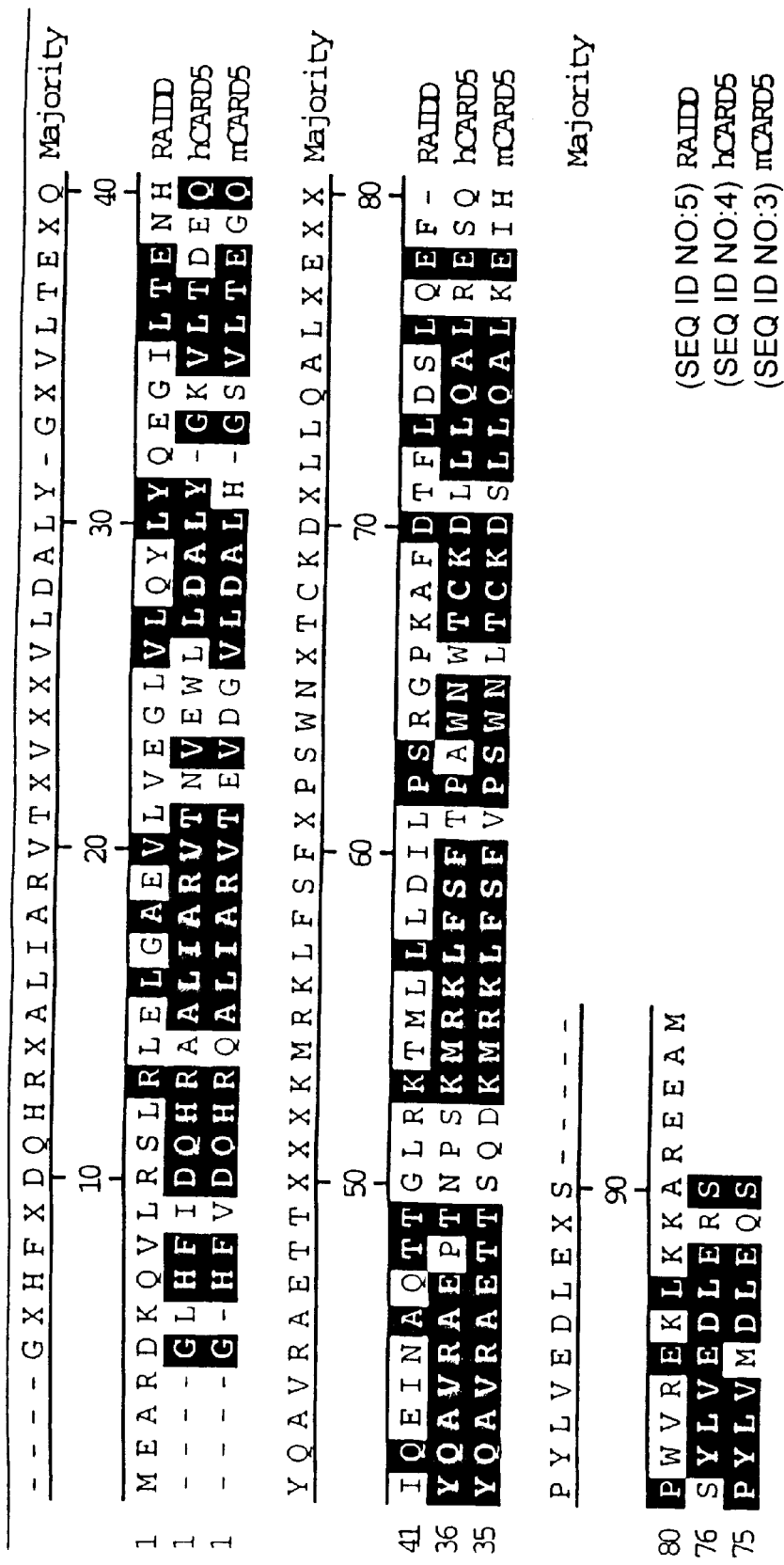
FIG. 7 depicts an alignment of the CARD domains of murine CARD-5 (SEQ ID NO:7), human CARD-5 (SEQ ID NO:8), and RAIDD (SEQ ID NO:9). A consensus sequence is also depicted (SEQ ID NO:15).

A region, the CARD domain (SEQ ID NO:8), of human CARD-5 protein (SEQ ID NO:4) and a region, the CARD domain (SEQ ID NO:7), of murine CARD-5 protein (SEQ ID NO:2) bear some similarity to the CARD of RAIDD (SEQ ID NO:9). This comparison is depicted in FIG. 7.

CARD-5 is a member of a family of molecules (the "CARD-5 family") having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

In one embodiment, a CARD-5 protein includes a CARD domain having at least about 65%, preferably at least about 75%, and more preferably about 85%, 95%, or 98% amino acid sequence identity to the CARD domain of SEQ ID NO:7 or the CARD domain of SEQ ID NO:8.

Preferred CARD-5 polypeptides of the present invention have an amino acid sequence sufficiently identical to the CARD domain amino acid sequence of SEQ ID NO:7, SEQ ID NO:8.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "CARD-5 activity", "biological activity of CARD-5" or "functional activity of CARD-5", refers to an activity exerted by a CARD-5 protein, polypeptide or nucleic acid molecule on a CARD-5 responsive cell as determined in vivo, or in vitro, according to standard techniques. A CARD-5 activity can be a direct activity, such as an association with or an enzymatic activity on a second protein or an indirect activity, such as a cellular signaling activity mediated by interaction of the CARD-5 protein with a second protein.

In one embodiment, a CARD-5 activity includes at least one or more of the following activities: (i) the ability to interact with proteins in an apoptotic signaling pathway (ii) the ability to interact with a CARD-5 ligand; (iii) the ability to interact with an intracellular target protein; (iv) the ability to interact, directly or indirectly with one or more with caspases, e.g., caspase-1; (v) the ability to modulate the activity of a caspase, e.g., caspase-9; (vi) the ability to modulate the activity of NF-κB; (vii) the ability to modulate the activity of a stress activated kinase (e.g., JNK/p38). It is also possible that CARD-5 might have one or more of the following activities: (i) the ability to modulate Apaf-1; (ii) the ability to be modulated by a Bcl-2 family member; and (iii) the ability to be modulated by the p75 neurotrophin receptor. For example, in Example 2, CARD-5 was shown to bind the CARD domains of caspase-l, CARD-7, and CARD-5. In Example 3, CARD-5 was shown to induce NF-κB-mediated transcription.

CARD-5 may modulate caspase-1 activation by binding to caspase-1. CARD-5 binding to caspase-1 may effect an oligomerizaton-based activation of the molecule. This caspase-1 activation can lead to the activation of inflammatory and/or apoptotic pathways. Alternatively, CARD-5 binding of caspase-1 may attenuate caspase-1 activation mediated by other activator adaptors such as RIP2.

Accordingly, another embodiment of the invention features isolated CARD-5 proteins and polypeptides having a CARD-5 activity.

Various aspects of the invention are described in further detail in the following subsections.

I. Isolated Nucleic Acid Molecules

One aspect of the invention pertains to isolated nucleic acid molecules that encode CARD-5 proteins or biologically active portions thereof, as well as nucleic acid molecules sufficient for use as hybridization probes to identify CARD-5-encoding nucleic acids (e.g., CARD-5 mRNA) and fragments for use as PCR primers for the amplification or mutation of CARD-5 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one that is separated from other nucleic acid molecules that are present in the natural source of the nucleic acid. Preferably, an "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated CARD-5 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:4, SEQ ID NO:6, SEQ ID NO:1, SEQ ID NO:3, the cDNA of ATCC PTA-212, or the cDNA of ATCC PTA-213 or a complement of any of these nucleotide sequences, can be isolated using standard molecular biology techniques and the sequence information provided herein. Using all or portion of the nucleic acid sequences of SEQ ID NO:4, SEQ ID NO:6, SEQ ID NO:1, SEQ ID NO:3, the cDNA of ATCC PTA-212, or the cDNA of PTA-213, as a hybridization probe, CARD-5 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A nucleic acid of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to CARD-5 nucleotide sequences can be prepared by standard synthetic techniques, e.g., using an automated DNA synthesizer.

In another embodiment, an isolated nucleic acid molecule of the invention comprises a nucleic acid molecule which is a complement of the nucleotide sequence shown in SEQ ID NO:4, SEQ ID NO:6, SEQ ID NO:1, SEQ ID NO:3, the cDNA of PTA-212, or the cDNA of PTA-213, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, the nucleic acid molecule of the invention can comprise only a portion of a nucleic acid sequence encoding CARD-5, for example, a fragment which can be used as a probe or primer or a fragment encoding a biologically active portion of CARD-5. The nucleotide sequence determined from the cloning of the human CARD-5 allows for the generation of probes and primers designed for use in identifying and/or cloning CARD-5 homologues in other cell types, e.g., from other tissues, as well as CARD-5 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:4, SEQ ID NO:6, SEQ ID NO:1, SEQ ID NO:3, the cDNA of PTA-212, or the cDNA of PTA-213, or of a naturally occurring mutant of one of SEQ ID NO:4, SEQ ID NO:6, SEQ ID NO:1, SEQ ID NO:3, the cDNA of PTA-212, or the cDNA of PTA-213.

Probes based on the CARD-5 nucleotide sequence can be used to detect transcripts or genomic sequences encoding the same or similar proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the CARD-5 proteins of the present invention, identifying cells or tissue which misexpress a CARD-5 protein, such as by measuring a level of a CARD-5-encoding nucleic acid in a sample of cells from a subject, e.g., detecting CARD-5 mRNA levels or determining whether a genomic CARD-5 gene has been mutated or deleted.

A nucleic acid fragment encoding a "biologically active portion" of CARD-5 can be prepared by isolating a portion of SEQ ID NO:4, SEQ ID NO:6, SEQ ID NO:1, SEQ ID NO:3, the cDNA of PTA-212, or the cDNA of PTA-213, which encodes a polypeptide having a CARD-5 biological activity, expressing the encoded portion of CARD-5 protein (e.g., by recombinant expression in vitro) and assessing the activity of the encoded portion of CARD-5. For example, a nucleic acid fragment encoding a biologically active portion of CARD-5 includes a CARD domain, e.g., SEQ ID NO:7, or SEQ ID NO:8.

The invention further encompasses nucleic acid molecules that differ from the nucleotide sequence of SEQ ID NO:4, SEQ ID NO:6, SEQ ID NO:1, SEQ ID NO:3, the cDNA of PTA-212, or the cDNA of PTA-213, due to degeneracy of the genetic code and thus encode the same CARD-5 protein as that encoded by the nucleotide sequence shown in SEQ ID NO:4, SEQ ID NO:6, SEQ ID NO:1, SEQ ID NO:3, the cDNA of ATCC PTA-212, or the cDNA of ATCC PTA-213.

In addition to the CARD-5 nucleotide sequence shown in SEQ ID NO:4, SEQ ID NO:6, SEQ ID NO:1, SEQ ID NO:3, the cDNA of ATCC PTA-212, or the cDNA of ATCC PTA-213, it will be appreciated by those skilled in the art that DNA sequence polymorphisms that lead to changes in the amino acid sequences of CARD-5 may exist within a population (e.g., the human population). Such genetic polymorphism in the CARD-5 gene may exist among individuals within a population due to natural allelic variation. As used herein, the terms "gene" and "recombinant gene" refer to nucleic acid molecules comprising an open reading frame encoding a CARD-5 protein, preferably a mammalian CARD-5 protein. Such natural allelic variations can typically result in 1–5% variance in the nucleotide sequence of the CARD-5 gene. Any and all such nucleotide variations and resulting amino acid polymorphisms in CARD-5 that are the result of natural allelic variation and that do not alter the functional activity of CARD-5 are intended to be within the scope of the invention. Thus, e.g., 1%, 2%, 3%, 4%, or 5% of the amino acids in CARD-5 are replaced by another amino acid, preferably the amino acids are replaced by conservative substitutions.

Moreover, nucleic acid molecules encoding CARD-5 proteins from other species (CARD-5 orthologs/homologues), which have a nucleotide sequence which differs from that of a CARD-5 disclosed herein, are intended to be within the scope of the invention.

In yet another embodiment, an isolated nucleic acid molecule of the invention is at least 300 (350, 400, 450, 500, 550, 600, 650, 700, or 740) nucleotides in length and hybridizes under stringent conditions to a nucleic acid molecule consisting of the nucleotide sequence of SEQ ID NO:4 or SEQ ID NO:6.

In yet another embodiment, an isolated nucleic acid molecule of the invention is at least 300 (350, 400, 450, 500, 550, 600, 650, 700, or 761) nucleotides in length and hybridizes under stringent conditions to a nucleic acid molecule consisting of the nucleotide sequence of SEQ ID NO:1 or SEQ ID NO:3.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. An, non-limiting example of stringent hybridization conditions are hybridization in 6× sodium chloride/sodium citrate (SSC) at about 45° C., followed by one or more washes in 0.2× SSC, 0.1% SDS at 50–65° C. (e.g., 50° C. or 60° C. or 65° C.). Preferably, the isolated nucleic acid molecule of the invention that hybridizes under stringent conditions corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the CARD-5 sequence that may exist in the population, the skilled artisan will further appreciate that changes can be introduced by mutation into the nucleotide sequence of SEQ ID NO:4, SEQ ID NO:6, SEQ ID NO:1, SEQ ID NO:3, the cDNA of ATCC PTA-212, or the cDNA of ATCC PTA-213, thereby leading to changes in the amino acid sequence of the encoded protein without altering the functional ability of the protein. For example, one can make nucleotide substitutions leading to amino acid substitutions at "non-essential" amino acid residues. A "non-essential" amino acid residue is a residue that can be altered from the wild-type sequence of human CARD-5 protein or murine CARD-5 protein without altering the biological activity, whereas an "essential" amino acid residue is required for biological activity. For example, amino acid residues that are conserved among CARD-5 proteins of various species are predicted to be particularly unamenable to alteration.

For example, preferred CARD-5 proteins of the present invention, contain at least one CARD domain. A CARD domain contains at least one nucleotide binding domain or Leucine-rich repeats. Such conserved domains are less likely to be amenable to mutation. Other amino acid residues, however, (e.g., those that are not conserved or only semi-conserved among CARD-5 of various species) may not be essential for activity and thus are likely to be amenable to alteration.

Accordingly, another aspect of the invention pertains to nucleic acid molecules encoding CARD-5 proteins that contain changes in amino acid residues that are not essential for activity. Such CARD-5 proteins differ in amino acid sequence from SEQ ID NO:5 or SEQ ID NO:2, and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:5 or SEQ ID NO:2.

An isolated nucleic acid molecule encoding a CARD-5 protein having a sequence which differs from that of SEQ ID NO:4, SEQ ID NO:6, SEQ ID NO:1, SEQ ID NO:3 the cDNA of ATCC PTA-212, or the cDNA of ATCC PTA-213, can be created by introducing one or more nucleotide substitutions, additions or deletions into the nucleotide sequence of murine CARD-5 (SEQ ID NO:1, SEQ ID NO:3, the cDNA of PTA-211), or human CARD-5 (SEQ ID NO:4, SEQ ID NO:6, the cDNA of ATCC PTA-213), such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in CARD-5 is preferably replaced with another amino acid residue from the same side chain family. Alternatively, mutations can be introduced randomly along all or part of a CARD-5 coding sequence, such as by saturation mutagenesis, and the resultant mutants can be screened for CARD-5 biological activity to identify mutants that retain activity. Following mutagenesis, the encoded protein can be expressed recombinantly and the activity of the protein can be determined.

In an embodiment, a mutant CARD-5 protein can be assayed for: (1) the ability to form protein:protein interactions with proteins in the apoptotic signaling pathway; (2) the ability to bind a CARD-5 ligand; or (3) the ability to bind to an intracellular target protein. For example, (1) in Example 3, a two-hybrid screening assay for the physical interaction of CARD-5 and caspase-1, CARD-7, CARD-12, or CARD-5 is shown. In yet another embodiment, a mutant CARD-5 protein can be assayed for the ability to modulate cellular proliferation, cellular differentiation, or cellular death. For example, in Example 4, an assay for the regulation of the NF-κB pathway by CARD-5 is described.

The present invention encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CARD-5 coding strand, or to only a portion thereof, e.g., all or part of the protein coding region (or open reading frame). An antisense nucleic acid molecule can be antisense to a noncoding region of the coding strand of a nucleotide sequence encoding CARD-5. The noncoding regions ("5' and 3' untranslated regions") are the 5' and 3' sequences which flank the coding region and are not translated into amino acids. Given the coding strand sequences encoding CARD-5 disclosed herein, antisense nucleic acids of the invention can be designed according to the rules of Watson and Crick base pairing. The antisense nucleic acid molecule can be complementary to the entire coding region of CARD-5 mRNA, but more preferably is an oligonucleotide which is antisense to only a portion of the coding or noncoding region of CARD-5 mRNA. For example, the antisense oligonucleotide can be complementary to the region surrounding the translation start site of the human CARD-5 mRNA, e.g., TAGGACCTCGGTAC-CCGCGCGCGCG (SEQ ID NO:16) or CGCCGGCCCC TAGGACCTCGGTACC (SEQ ID NO:17). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a CARD-5 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave CARD-5 mRNA transcripts to thereby inhibit translation of CARD-5 mRNA. A ribozyme having specificity for a CARD-5-encoding nucleic acid can be designed based upon the nucleotide sequence of a CARD-5 cDNA disclosed herein. For example, a derivative of a Tetrahymena L-19 IVS RNA can be constructed in which the nucleotide sequence of the active site is complementary to the nucleotide sequence to be cleaved in a CARD-5-encoding mRNA. See, e.g., Cech et al. U.S. Pat. No. 4,987,071; and Cech et al. U.S. Pat. No. 5,116,742. Alternatively, CARD-5 mRNA can be used to select a catalytic RNA having a specific ribonuclease activity from a pool of RNA molecules. See, e.g., Bartel and Szostak (1993) Science 261:1411–1418.

The invention also encompasses nucleic acid molecules which form triple helical structures. For example, CARD-5 gene expression can be inhibited by targeting nucleotide sequences complementary to the regulatory region of the CARD-5 (e.g., the CARD-5 promoter and/or enhancers) to form triple helical structures that prevent transcription of the CARD-5 gene in target cells. See generally, Helene (1991) Anticancer Drug Des. 6(6):569–84; Helene (1992) Ann. N.Y. Acad. Sci. 660:27–36; and Maher (1992) Bioassays 14(12):807–15.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670–675.

PNAs of CARD-5 can be used for therapeutic and diagnostic applications. For example, PNAs can be used as antisense or antigene agents for sequence-specific modulation of gene expression by, e.g., inducing transcription or translation arrest or inhibiting replication. PNAs of CARD-5 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670–675).

In another embodiment, PNAs of CARD-5 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of CARD-5 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63). Alternatively, chimeric molecules can be synthesized with a 5' DNA segment and a 3' PNA segment (Peterser et al. (1975) Bioorganic Med. Chem. Lett. 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated CARD-5 Proteins and Anti-CARD-5 Antibodies.

One aspect of the invention pertains to isolated CARD-5 proteins, and biologically active portions thereof, as well as polypeptide fragments suitable for use as immunogens to raise anti-CARD-5 antibodies. In one embodiment, native CARD-5 proteins can be isolated from cells or tissue sources by an appropriate purification scheme using standard protein purification techniques. In another embodiment, CARD-5 proteins are produced by recombinant DNA techniques. Alternative to recombinant expression, a CARD-5 protein or polypeptide can be synthesized chemically using standard peptide synthesis techniques.

An "isolated" or "purified" protein or biologically active portion thereof is substantially free of cellular material or other contaminating proteins from the cell or tissue source from which the CARD-5 protein is derived, or substantially free from chemical precursors or other chemicals when chemically synthesized. The language "substantially free of cellular material" includes preparations of CARD-5 protein in which the protein is separated from cellular components of the cells from which it is isolated or recombinantly produced. Thus, CARD-5 protein that is substantially free of cellular material includes preparations of CARD-5 protein having less than about 30%, 20%, 10%, or 5% (by dry weight) of non-CARD-5 protein (also referred to herein as a "contaminating protein"). When the CARD-5 protein or biologically active portion thereof is recombinantly produced, it is also preferably substantially free of culture medium, i.e., culture medium represents less than about 20%, 10%, or 5% of the volume of the protein preparation. When CARD-5 protein is produced by chemical synthesis, it is preferably substantially free of chemical precursors or other chemicals, i.e., it is separated from chemical precursors or other chemicals which are involved in the synthesis of the protein. Accordingly such preparations of CARD-5 protein have less than about 30%, 20%, 10%, 5% (by dry weight) of chemical precursors or non-CARD-5 chemicals.

Biologically active portions of a CARD-5 protein include peptides comprising amino acid sequences sufficiently identical to or derived from the amino acid sequence of the CARD-5 protein (e.g., the amino acid sequence shown in SEQ ID NO:5 SEQ ID NO:2), which include less amino acids than the full length CARD-5 protein, and exhibit at least one activity of a CARD-5 protein. Typically, biologically active portions comprise a domain or motif with at least one activity of the CARD-5 protein. A biologically active portion of a CARD-5 protein can be a polypeptide which is, for example, 10, 25, 50, 100 or more amino acids in length. Preferred biologically active polypeptides include one or more identified CARD-5 structural domains, e.g., the CARD domain.

Moreover, other biologically active portions, in which other regions of the protein are deleted, can be prepared by recombinant techniques and evaluated for one or more of the functional activities of a native CARD-5 protein.

CARD-5 protein has the amino acid sequence shown of SEQ ID NO:5, or SEQ ID NO:2. Other useful CARD-5 proteins are substantially identical to SEQ ID NO:5, SEQ ID NO:2, and retain the functional activity of the protein of SEQ ID NO:5, or SEQ ID NO:2, yet differ in amino acid sequence due to natural allelic variation or mutagenesis. In Example 2, CARD-5 is shown to bind to the CARD domain of caspase-1.

A useful CARD-5 protein is a protein which includes an amino acid sequence at least about 45%, preferably 55%, 65%, 75%, 85%, 95%, or 99% identical to the amino acid sequence of SEQ ID NO:5, SEQ ID NO:2, and retains the functional activity of the CARD-5 proteins of SEQ ID NO:5, SEQ ID NO:2.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=of identical positions/total of positions× 100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to CARD-5 nucleic acid molecules of the invention. For example, the TBLASTN program can be used to query a database of sequences of full length and partial cDNA sequences with the human CARD-5 polypeptide sequence and BLASTN can be used to query a proprietary EST database with the 5' untranslated sequence of CARD-5. BLAST protein searches can be performed with the XBLAST program, score=50, wordlength=3 to obtain amino acid sequences homologous to CARD-5 protein molecules of the invention. To obtain gapped alignments for comparison purposes, Gapped BLAST can be utilized as described in Altschul et al. (1997) Nucleic Acids Res. 25:3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically exact matches are counted.

The invention also provides CARD-5 chimeric or fusion proteins. As used herein, a CARD-5 "chimeric protein" or "fusion protein" comprises a CARD-5 polypeptide operatively linked to a non-CARD-5 polypeptide. A "CARD-5 polypeptide" refers to a polypeptide having an amino acid sequence corresponding to all or a portion (preferably a biologically active portion) of a CARD-5, whereas a "non-CARD-5 polypeptide" refers to a polypeptide having an amino acid sequence corresponding to a protein which is not substantially identical to the CARD-5 protein, e.g., a protein which is different from the CARD-5 proteins and which is derived from the same or a different organism. Within the fusion protein, the term "operatively linked" is intended to indicate that the CARD-5 polypeptide and the non-CARD-5 polypeptide are fused in-frame to each other. The heterologous polypeptide can be fused to the N-terminus or C-terminus of the CARD-5 polypeptide.

One useful fusion protein is a GST fusion protein in which the CARD-5 sequences are fused to the C-terminus of the GST sequences. Such fusion proteins can facilitate the purification of recombinant CARD-5. In another embodiment, the fusion protein contains a signal sequence from another protein. In certain host cells (e.g., mammalian host cells), expression and/or secretion of CARD-5 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al., second edition, Cold Spring Harbor Laboratory Press, 1989) and the protein A secretory signal (Pharmacia Biotech; Piscataway, N.J.).

In yet another embodiment, the fusion protein is a CARD-5-immunoglobulin fusion protein in which all or part of CARD-5 is fused to sequences derived from a member of the immunoglobulin protein family. The CARD-5-immunoglobulin fusion proteins of the invention can be incorporated into pharmaceutical compositions and administered to a subject to inhibit an interaction between a CARD-5 ligand and a CARD-5 protein on the surface of a cell, to thereby suppress CARD-5-mediated signal transduction in vivo. The CARD-5-immunoglobulin fusion proteins can be used to affect the bioavailability of a CARD-5 cognate ligand. Inhibition of the CARD-5 ligand/CARD-5 interaction may be useful therapeutically for both the treatment of proliferative and differentiative disorders, as well as modulating (e.g., promoting or inhibiting) cell survival. Moreover, the CARD-5-immunoglobulin fusion proteins of the invention can be used as immunogens to produce anti-CARD-5 antibodies in a subject, to purify CARD-5 ligands and in screening assays to identify molecules which inhibit the interaction of CARD-5 with a CARD-5 ligand.

Preferably, a CARD-5 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A CARD-5-encoding nucleic acid can be cloned into such an expression vector such that the fusion moiety is linked in-frame to the CARD-5 protein.

The present invention also pertains to variants of the CARD-5 proteins which function as either CARD-5 agonists (mimetics) or as CARD-5 antagonists. Variants of the CARD-5 protein can be generated by mutagenesis, e.g., discrete point mutation or truncation of the CARD-5 protein. An agonist of the CARD-5 protein can retain substantially the same, or a subset, of the biological activities of the naturally occurring form of the CARD-5 protein. An antagonist of the CARD-5 protein can inhibit one or more of the activities of the naturally occurring form of the CARD-5 protein by, for example, competitively binding to a downstream or upstream member of a cellular signaling cascade which includes the CARD-5 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the CARD-5 proteins.

Variants of the CARD-5 protein which function as either CARD-5 agonists (mimetics) or as CARD-5 antagonists can be identified by screening combinatorial libraries of mutants, e.g., truncation mutants of the CARD-5 protein for CARD-5 protein agonist or antagonist activity. In one embodiment, a variegated library of CARD-5 variants is generated by combinatorial mutagenesis at the nucleic acid level and is encoded by a variegated gene library. A variegated library of CARD-5 variants can be produced by, for example, enzymatically ligating a mixture of synthetic oligonucleotides into gene sequences such that a degenerate set of potential CARD-5 sequences is expressible as individual polypeptides, or alternatively, as a set of larger fusion proteins (e.g., for phage display) containing the set of CARD-5 sequences therein. There are a variety of methods which can be used to produce libraries of potential CARD-5 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CARD-5 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

Useful fragments of CARD-5 include fragments comprising or consisting of a domain or subdomain described herein, e.g., a kinase domain or a CARD domain.

In addition, libraries of fragments of the CARD-5 protein coding sequence can be used to generate a variegated population of CARD-5 fragments for screening and subsequent selection of variants of a CARD-5 protein. In one embodiment, a library of coding sequence fragments can be generated by treating a double stranded PCR fragment of a CARD-5 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the CARD-5 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CARD-5 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify CARD-5 variants (Arkin and Yourvan (1992) Proc. Natl. Acad. Sci. USA 89:7811–7815; Delgrave et al. (1993) Protein Engineering 6(3):327–331).

An isolated CARD-5 protein, or a portion or fragment thereof, can be used as an immunogen to generate antibodies that bind CARD-5 using standard techniques for polyclonal and monoclonal antibody preparation. The full-length CARD-5 protein can be used or, alternatively, the invention provides antigenic peptide fragments of CARD-5 for use as immunogens. The antigenic peptide of CARD-5 comprises at least 8 (preferably 10, 15, 20, or 30) amino acid residues of the amino acid sequence shown in SEQ ID NO:5 or SEQ ID NO:2 or polypeptides including amino acids 128–139 or 287–298 of human CARD-5 and encompasses an epitope of CARD-5 such that an antibody raised against the peptide forms a specific immune complex with CARD-5.

Useful antibodies include antibodies which bind to a domain or subdomain of CARD-5 described herein (e.g., a kinase domain, a CARD domain, or a leucine-rich domain).

Preferred epitopes encompassed by the antigenic peptide are regions of CARD-5 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm.

A CARD-5 immunogen typically is used to prepare antibodies by immunizing a suitable subject, (e.g., rabbit, goat, mouse or other mammal) with the immunogen. An appropriate immunogenic preparation can contain, for example, recombinantly expressed CARD-5 protein or a chemically synthesized CARD-5 polypeptide. The preparation can further include an adjuvant, such as Freund's complete or incomplete adjuvant, or similar immunostimulatory agent. Immunization of a suitable subject with an immunogenic CARD-5 preparation induces a polyclonal anti-CARD-5 antibody response.

Accordingly, another aspect of the invention pertains to anti-CARD-5 antibodies. The term "antibody" as used herein refers to immunoglobulin molecules and immunologically active portions of immunoglobulin molecules, i.e., molecules that contain an antigen binding site which specifically binds an antigen, such as CARD-5. A molecule which specifically binds to CARD-5 is a molecule which binds CARD-5, but does not substantially bind other molecules in a sample, e.g., a biological sample, which naturally contains CARD-5. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind CARD-5. The term "monoclonal antibody" or "monoclonal antibody composition", as used herein, refers to a population of antibody molecules that contain only one species of an antigen binding site capable of immunoreacting with a particular epitope of CARD-5. A monoclonal antibody composition thus typically displays a single binding affinity for a particular CARD-5 protein with which it immunoreacts.

Polyclonal anti-CARD-5 antibodies can be prepared as described above by immunizing a suitable subject with a CARD-5 immunogen. The anti-CARD-5 antibody titer in the immunized subject can be monitored over time by standard techniques, such as with an enzyme linked immunosorbent assay (ELISA) using immobilized CARD-5. If desired, the antibody molecules directed against CARD-5 can be isolated from the mammal (e.g., from the blood) and further purified by well-known techniques, such as protein A chromatography to obtain the IgG fraction. At an appropriate time after immunization, e.g., when the anti-CARD-5 antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a CARD-5 immunogen as described above, and the culture supernatants of the resulting hybridoma cells are screened to identify a hybridoma producing a monoclonal antibody that binds CARD-5.

Any of the many well known protocols used for fusing lymphocytes and immortalized cell lines can be applied for the purpose of generating an anti-CARD-5 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387–402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4–1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CARD-5, e.g., using a standard ELISA assay.

Alternative to preparing monoclonal antibody-secreting hybridomas, a monoclonal anti-CARD-5 antibody can be identified and isolated by screening a recombinant combinatorial immunoglobulin library (e.g., an antibody phage display library) with CARD-5 to thereby isolate immunoglobulin library members that bind CARD-5. Kits for generating and screening phage display libraries are commercially available (e.g., the Pharmacia Recombinant Phage Antibody System, Catalog No. 27–9400–01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant anti-CARD-5 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, (1985) Science 229:1202–1207; Oi et al. (1986) Bio/Techniques 4:214; U.S. Pat. No. 5,225,539; Jones et al. (1986) Nature 321:552–525; Verhoeyan et al. (1988) Science 239:1534; and Beidler et al. (1988) J. Immunol. 141:4053–4060.

An anti-CARD-5 antibody (e.g., monoclonal antibody) can be used to isolate CARD-5 by standard techniques, such as affinity chromatography or immunoprecipitation. An anti-CARD-5 antibody can facilitate the purification of natural CARD-5 from cells and of recombinantly produced CARD-5 expressed in host cells. Moreover, an anti-CARD-5 antibody can be used to detect CARD-5 protein (e.g., in a cellular lysate or cell supernatant) in order to evaluate the abundance and pattern of expression of the CARD-5 protein. Anti-CARD-5 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding CARD-5 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CARD-5 proteins, mutant forms of CARD-5, fusion proteins, etc.).

The recombinant expression vectors of the invention can be designed for expression of CARD-5 in prokaryotic or eukaryotic cells, e.g., bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident $\lambda$ prophage harboring a T7 gn1 gene under the transcriptional control of the lacUV5 promoter.

One strategy to maximize recombinant protein expression in *E. coli* is to express the protein in a host bacteria with an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) Nucleic Acids Res. 20:2111–2118). Such alteration of nucleic acid sequences of the invention can be carried out by standard DNA synthesis techniques.

In another embodiment, the CARD-5 expression vector is a yeast expression vector. Examples of vectors for expression in yeast *S. cerivisae* include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall, (1993) Yeast 9:1299–1308), pYPGE15 (Brunelli and Pall, (1993) Yeast 9:1309–1318), pACTII (Dr. S. E. Elledge, Baylor College of Medicine), and picZ (InVitrogen Corp, San Diego, Calif.). Alternatively, CARD-5 can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840), pCI (Promega), and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al.

(1985) Science 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CARD-5 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention or isolated nucleic acid molecule of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, CARD-5 protein can be expressed in bacterial cells such as E. coli, insect cells, yeast or mammalian cells (such as Chinese hamster ovary cells (CHO) or COS cells). Other suitable host cells are known to those skilled in the art. For example, in Examples 2 and 4, a 293T host cell for expression of CARD-5 or fragments thereof are described.

Vector DNA or an isolated nucleic acid molecule of the invention can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule of the invention carried by the vector. In some cases, and isolated nucleic acid molecule of the invention is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding CARD-5 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a CARD-5 protein. Accordingly, the invention further provides methods for producing CARD-5 protein using the host cells of the invention. In one embodiment, the method comprises culturing the host cell of the invention (into which a recombinant expression vector or isolated nucleic acid molecule encoding CARD-5 has been introduced) in a suitable medium such that CARD-5 protein is produced. In another embodiment, the method further comprises isolating CARD-5 from the medium or the host cell.

The host cells of the invention can also be used to produce nonhuman transgenic animals. For example, in one embodiment, a host cell of the invention is a fertilized oocyte or an embryonic stem cell into which CARD-5-coding sequences have been introduced. Such host cells can then be used to create non-human transgenic animals in which exogenous CARD-5 sequences have been introduced into their genome or homologous recombinant animals in which endogenous CARD-5 sequences have been altered. Such animals are useful for studying the function and/or activity of CARD-5 and for identifying and/or evaluating modulators of CARD-5 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous CARD-5 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CARD-5-encoding nucleic acid into the male pronuclei of a fertilized oocyte, e.g., by microinjection, retroviral infection, and allowing the oocyte to develop in a pseudopregnant female foster animal. The CARD-5 cDNA sequence, e.g., that of SEQ ID NO:4, SEQ ID NO:6, SEQ ID NO:1, SEQ ID NO:3, or the cDNA of ATCC PTA-212, or the cDNA of ATCC PTA-213 can be introduced as a transgene into the genome of a non-human animal. Alternatively, a nonhuman homolog or ortholog of the human CARD-5 gene, such as a mouse CARD-5 gene, can be isolated based on hybridization to the human CARD-5 cDNA and used as a transgene. A tissue-specific regulatory sequence(s) can be operably linked to the CARD-5 transgene to direct expression of CARD-5 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the CARD-5 transgene in its genome and/or expression of CARD-5 mRNA in tissues or cells of the animals. A transgenic founder animal can then be used to breed additional animals carrying the transgene. Moreover, transgenic animals carrying a transgene encoding CARD-5 can further be bred to other transgenic animals carrying other transgenes.

To create an homologous recombinant animal, a vector is prepared which contains at least a portion of a CARD-5 gene (e.g., a human or a non-human homolog of the CARD-5 gene, e.g., a murine CARD-5 gene) into which a deletion, addition or substitution has been introduced to thereby alter, e.g., functionally disrupt, the CARD-5 gene. In an embodiment, the vector is designed such that, upon homologous recombination, the endogenous CARD-5 gene is functionally disrupted (i.e., no longer encodes a functional protein; also referred to as a "knock out" vector). Alternatively, the vector can be designed such that, upon homologous recombination, the endogenous CARD-5 gene is mutated or otherwise altered but still encodes functional protein (e.g., the upstream regulatory region can be altered to thereby alter the expression of the endogenous CARD-5 protein). In the homologous recombination vector, the altered portion of the CARD-5 gene is flanked at its 5' and 3' ends by additional nucleic acid of the CARD-5 gene to allow for homologous recombination to occur between the exogenous CARD-5 gene carried by the vector and an endogenous CARD-5 gene in an embryonic stem cell. The additional flanking CARD-5 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced CARD-5 gene has homologously recombined with the endogenous CARD-5 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of *Saccharomyces cerevisiae* (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double"transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The CARD-5 nucleic acid molecules, CARD-5 proteins, and anti-CARD-5 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a polypeptide or nucleic acid of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid of the invention and one or more addtional active compounds.

The agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight les than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may) for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CARD-5 protein or anti-CARD-5 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology), c) predictive medicine (e.g., diagnostic assays, prognostic assays, monitoring clinical trials, and pharmacogenomics); and d) methods of treatment (e.g., therapeutic and prophylactic). A CARD-5 protein interacts with other cellular proteins and can thus be used for (i) regulation of cellular proliferation; (ii) regulation of cellular differentiation; and (iii) regulation of cell survival. The isolated nucleic acid molecules of the invention can be used to express CARD-5 protein (e.g., via a recombinant expression vector in a host cell in gene therapy applications), to detect CARD-5 mRNA (e.g., in a biological sample) or a genetic lesion in a CARD-5 gene, and to modulate CARD-5 activity. In addition, the CARD-5 proteins can be used to screen drugs or compounds which modulate the CARD-5 activity or expression as well as to treat disorders characterized by insufficient or excessive production of CARD-5 protein or production of CARD-5 protein forms which have decreased or aberrant activity compared to CARD-5 wild type protein. In addition, the anti-CARD-5 antibodies of the invention can be used to detect and isolate CARD-5 proteins and modulate CARD-5 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to CARD-5 proteins or biologically active portions thereof or have a stimulatory or inhibitory effect on, for example, CARD-5 expression or CARD-5 activity. An example of a biologically active portion of human CARD-5 is amino acids 111–881 (SEQ ID NO:8) encoding the CARD domain.

Among the screening assays provided by the invention are screening to identify molecules that prevent the dimerization of a CARD-containing polypeptide of the invention, screening to identify molecules which block the binding of a CARD containing polypeptide to a CARD-containing polypeptide of the invention (e.g., CARD-5), screening to identify a competitive inhibitor of the binding of a nucleotide to the nucleotide binding site of a CARD-containing polypeptide of the invention, e.g., human CARD-5, screening to identify compounds which block the interaction between the leucine-rich repeat of a CARD-containing polypeptide of the invention and a ligand which binds to the leucine-rich repeat.

For nucleotide binding site-containing polypeptides of the invention, screening assays can be used to identify molecules that modulate the activity of the nucleotide binding site.

For example, molecules can be tested for their ability to modulate, e.g., antagonize, the hydrolysis of ATP by the nucleotide binding site of a polypeptide of the invention. Methods of detecting the hydrolysis of ATP by a nucleotide binding site are described in, for example, Gadsby et al., Physiol. Rev. 79:S77–S107, 1999.

For CARD-5, screening assays can be used to identify molecules that interfere with the interaction between the CARD domain of CARD-5 and a CARD-5 ligand, e.g., caspase-1, CARD-7, CARD-12, or CARD-5. Additionally, screening assays can be used to identify molecules that modulate a CARD-5-mediated increase in transcription of genes having an NF-κB binding site.

In one embodiment, the invention provides assays for screening candidate or test compounds which bind to or modulate the activity of a CARD-5 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (Patent Nos. 5,571,698; 5,403,484; and 5,223,409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

Determining the ability of the test compound to modulate the activity of CARD-5 or a biologically active portion thereof can be accomplished, for example, by determining the ability of the CARD-5 protein to bind to or interact with a CARD-5 target molecule. As used herein, a "target molecule" is a molecule with which a CARD-5 protein binds or interacts in nature, for example, a molecule associated with the internal surface of a cell membrane or a cytoplasmic molecule. A CARD-5 target molecule can be a non-CARD-5 molecule or a CARD-5 protein or polypeptide of the present invention. In one embodiment, a CARD-5 target molecule is a component of an apoptotic signal transduction pathway. The target, for example, can be a second intracellular protein which has catalytic activity or a protein which facilitates the association of downstream signaling molecules with CARD-5. In another embodiment, CARD-5 target molecules include caspase-1, CARD-7, CARD-12 and CARD-5 because these were each found to bind to CARD-5 (Example 3).

Determining the ability of the test compound to modulate the activity of CARD-5 or a biologically active portion thereof can be accomplished, for example, by determining the ability of the CARD-5 protein to bind to or interact with any of the specific proteins listed in the previous paragraph as CARD-5 target molecules. In another embodiment, CARD-5 target molecules include all proteins that bind to a CARD-5 protein or a fragment thereof in a two-hybrid system binding assay which can be used without undue experimentation to isolate such proteins from cDNA or genomic two-hybrid system libraries. For example, Example 3 describes the use of the CARD-5 CARD domain region to identify caspase-1, CARD-7, and CARD-5 in a two-hybrid screen. The binding assays described in this section can be cell-based or cell free (described subsequently).

Determining the ability of the CARD-5 protein to bind to or interact with a CARD-5 target molecule can be accomplished by one of the methods described above for determining direct binding. In an embodiment, determining the ability of the CARD-5 protein to bind to or interact with a CARD-5 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a CARD-5-responsive regulatory element operatively linked to a nucleic acid encoding a detectable marker, e.g. luciferase), or detecting a cellular response, for example, cell survival, cellular differentiation, or cell proliferation. For example, genes induced by CARD-5 expression can be identified by expressing CARD-5 in a cell line and conducting a transcriptional profiling experiment wherein the mRNA expression patterns of the cell line transformed with an empty expression vector and the cell line transformed with a CARD-5 expression vector are compared. The promoters of genes induced by CARD-5 expression can be operatively linked to reporter genes suitable for screening such as luciferase, secreted alkaline phosphatase, or beta-galactosidase and the resulting constructs could be introduced into appropriate expression vectors. A recombinant cell line containing CARD-5 and transfected with an expression vector containing a CARD-5 responsive promoter operatively linked to a reporter gene can be used to identify test compounds that modulate CARD-5 activity by assaying the expression of the reporter gene in response to contacting the recombinant cell line with test compounds. CARD-5 agonists can be identified as increasing the expression of the reporter gene and CARD-5 antagonists can be identified as decreasing the expression of the reporter gene.

In another embodiment of the invention, the ability of a test compound to modulate the activity of CARD-5 or biologically active portions thereof can be determined by assaying the ability of the test compound to modulate CARD-5-dependent pathways or processes where the CARD-5 target proteins that mediate the CARD-5 effect are known or unknown. Potential CARD-5-dependent pathways or processes include, but are not limited to, the modulation of cellular signal transduction pathways and their related second messenger molecules (e.g., intracellular $Ca^{2+}$, diacylglycerol, IP3, cAMP etc.), cellular enzymatic activities, cellular responses (e.g., cell survival, cellular differentiation, or cell proliferation), or the induction or repression of cellular or heterologous mRNAs or proteins. CARD-5-dependent pathways or processes could be assayed by standard cell-based or cell free assays appropriate for the specific pathway or process under study. For example, Example 4 describes how expression of CARD-5 in 293T cells induces the NF-κB pathway as determined by the measurement of a cotransfected NF-κB pathway luciferase reporter gene. In another embodiment, cells cotransfected with CARD-5 and the NF-κB luciferase reporter gene could be contacted with a test compound and test compounds that block CARD-5 activity could be identified by their reduction of CARD-5-dependent NF-κB pathway luciferase reporter gene expression. Test compounds that agonize CARD-5 would be expected to increase reporter gene expression. In another embodiment, CARD-5 could be expressed in a cell line and the recombinant CARD-5-expressing cell line could be contacted with a test compound. Test compounds that inhibit CARD-5 activity could be identified by their reduction of CARD-5-dependent NF-κB pathway stimulation as measured by the assay of a NF-κB pathway reporter gene, NF-κB nuclear localization, IκB phosphorylation or proteolysis, or other standard assays for NF-κB pathway activation known to those skilled in the art.

In yet another embodiment, an assay of the present invention is a cell-free assay comprising contacting a CARD-5 protein or biologically active portion thereof with a test compound and determining the ability of the test compound to bind to the CARD-5 protein or biologically active portion thereof. Binding of the test compound to the CARD-5 protein can be determined either directly or indirectly as described above. In one embodiment, a competitive binding assay includes contacting the CARD-5 protein or biologically active portion thereof with a compound known to bind CARD-5 to form an assay mixture, contacting the assay mixture with a test compound, and determining the ability of the test compound to interact with a CARD-5 protein, wherein determining the ability of the test compound to interact with a CARD-5 protein comprises determining the ability of the test compound to preferentially bind to CARD-5 or biologically active portion thereof as compared to the known binding compound.

In another embodiment, an assay is a cell-free assay comprising contacting CARD-5 protein or biologically active portion thereof with a test compound and determining the ability of the test compound to modulate (e.g., stimulate or inhibit) the activity of the CARD-5 protein or biologically active portion thereof. Determining the ability of the test compound to modulate the activity of CARD-5 can be accomplished, for example, by determining the ability of the CARD-5 protein to bind to a CARD-5 target molecule by one of the methods described above for determining direct binding. In an alternative embodiment, determining the ability of the test compound to modulate the activity of CARD-5 can be accomplished by determining the ability of the CARD-5 protein to further modulate a CARD-5 target molecule. For example, the catalytic/enzymatic activity of the target molecule on an appropriate substrate can be determined as previously described.

In yet another embodiment, the cell-free assay comprises contacting the CARD-5 protein or biologically active portion thereof with a known compound which binds CARD-5 to form an assay mixture, contacting the assay mixture with a test compound, and determining the ability of the test compound to interact with a CARD-5 protein, wherein determining the ability of the test compound to interact with a CARD-5 protein comprises determining the ability of the CARD-5 protein to preferentially bind to or modulate the activity of a CARD-5 target molecule. The cell-free assays of the present invention are amenable to use of both the soluble form or the membrane-associated form of CARD-5. A membrane-associated form of CARD-5 refers to CARD-5 that interacts with a membrane-bound target molecule. In the case of cell-free assays comprising the membrane-associated form of CARD-5, it may be desirable to utilize a solubilizing agent such that the membrane-associated form of CARD-5 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N, N-dimethyl-3-ammonio-1-propane sulfonate.

In more than one embodiment of the above assay methods of the present invention, it may be desirable to immobilize CARD-5 or its target molecule to facilitate separation of complexed from uncomplexed forms of one or both of the proteins, as well as to accommodate automation of the assay. Binding of a test compound to CARD-5, or interaction of CARD-5 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/CARD-5 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or CARD-5 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-5 binding or activity determined using standard techniques.

Other techniques for immobilizing proteins on matrices can also be used in the screening assays of the invention. For example, CARD-5 or its target molecule can be immobilized utilizing conjugation of biotin and streptavidin. Biotinylated CARD-5 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with CARD-5 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the CARD-5 or target molecule, as well as enzyme-linked assays which rely on detecting an enzymatic activity associated with the CARD-5 or target molecule.

In another embodiment, modulators of CARD-5 expression are identified in a method in which a cell is contacted with a candidate compound and the expression of the CARD-5 promoter, mRNA or protein in the cell is determined. The level of expression of CARD-5 mRNA or protein in the presence of the candidate compound is compared to the level of expression of CARD-5 mRNA or protein in the absence of the candidate compound. The candidate compound can then be identified as a modulator of CARD-5 expression based on this comparison. For example, when expression of CARD-5 mRNA or protein is greater (statistically significantly greater) in the presence of the candidate compound than in its absence, the candidate compound is identified as a stimulator of CARD-5 mRNA or protein expression. Alternatively, when expression of CARD-5 mRNA or protein is less (statistically significantly less) in the presence of the candidate compound than in its absence, the candidate compound is identified as an inhibitor of CARD-5 mRNA or protein expression. The level of CARD-5 mRNA or protein expression in the cells can be determined by methods described herein for detecting CARD-5 mRNA or protein. The activity of the CARD-5 promoter can be assayed by linking the CARD-5 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

In yet another aspect of the invention, the CARD-5 proteins can be used as "bait proteins" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with CARD-5 ("CARD-5-binding proteins" or "CARD-5-bp") and modulate CARD-5 activity. Such CARD-5-binding proteins are also likely to be involved in the propagation of signals by the CARD-5 proteins as, for example, upstream or downstream elements of the CARD-5 pathway. For example, Examples 2 and 3 describe the construction of a two-hybrid screening bait construct including human CARD-5 CARD domain and the use of this bait construct to screen a panel of 26 CARD domains, resulting in the identification of caspase-1, CARD-7, and CARD-5 as CARD-5 interacting proteins.

The two-hybrid system is based on the modular nature of most transcription factors, which consist of separable DNA-binding and activation domains. Briefly, the assay utilizes two different DNA constructs. In one construct, the gene that codes for CARD-5 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an CARD-5-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with CARD-5.

In an embodiment of the invention, the ability of a test compound to modulate the activity of CARD-5, or a biologically active portion thereof can be determined by assaying the ability of the test compound to block the binding of CARD-5 to its target proteins in a two-hybrid system assay. Examples 2 and 3 describe a two-hybrid system assay for the interaction between CARD-5 and its target proteins caspase-1, CARD-7, CARD-12 and CARD-5. To screen for test compounds that block the interaction between CARD-5 and its target proteins, which include but are not limited to caspase-1, CARD-7, and CARD-5, a yeast two-hybrid screening strain coexpressing the interacting bait and prey constructs, is contacted with the test compound and the activity of the two-hybrid system reporter gene, usually HIS3, lacZ, or URA3 is assayed. If the strain remains viable but exhibits a significant decrease in reporter gene activity, this would indicate that the test compound has inhibited the interaction between the bait and prey proteins. This assay could be automated for high throughput drug screening purposes. In another embodiment of the invention CARD-5 and its target proteins could be configured in the reverse two-hybrid system (Vidal et al. (1996) Proc. Natl. Acad. Sci. USA 93:10321–6 and Vidal et al. (1996) Proc. Natl. Acad. Sci. USA 93:10315–20) designed specifically for efficient drug screening. In the reverse two-hybrid system, inhibition of physical interaction with a target protein would result in induction of a reporter gene in contrast to the normal two-hybrid system where inhibition of CARD-5 physical interaction with a target protein would lead to reporter gene repression. The reverse two-hybrid system is preferred for drug screening because reporter gene induction is more easily assayed than report gene repression.

Alternative embodiments of the invention are proteins found to physically interact with proteins that bind to CARD-5. CARD-5 interactors could be configured into two-hybrid system baits and used in two-hybrid screens to identify additional members of the CARD-5 pathway. The interactors of CARD-5 interactors identified in this way could be useful targets for therapeutic intervention in CARD-5 related diseases and pathologies and an assay of their enzymatic or binding activity could be useful for the identification of test compounds that modulate CARD-5 activity.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, CARD-5 nucleic acid molecules described herein or fragments thereof, can be used to map the location of CARD-5 genes on a chromosome. The mapping of the CARD-5 sequences to chromosomes is an important first step in correlating these sequences with genes associated with disease.

Briefly, CARD-5 genes can be mapped to chromosomes by preparing PCR primers (preferably 15–25 bp in length) from the CARD-5 sequences. Computer analysis of CARD-5 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the CARD-5 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the CARD-5 sequences to design oligonucleotide primers, sublocalization can be achieved with panels of fragments from specific chromosomes. Other mapping strategies which can similarly be used to map a CARD-5 sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783–787.

Moreover, differences in the DNA sequences between individuals affected and unaffected with a disease associated with the CARD-5 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The CARD-5 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CARD-5 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CARD-5 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:4 and SEQ ID NO:1 can comfortably provide positive individual identification with a panel of perhaps 10 to 1,000 primers which each yield a noncoding amplified sequence of 100 bases. If predicted coding sequences, such as those in SEQ ID NO:6 and SEQ ID NO:3 are used, a more appropriate number of primers for positive individual identification would be 500–2,000.

If a panel of reagents from CARD-5 sequences described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:4 and SEQ ID NO:1 are particularly appropriate for this use as greater numbers of polymorphisms occur in the noncoding regions, making it easier to differentiate individuals using this technique. Examples of polynucleotide reagents include the CARD-5 sequences or portions thereof, e.g., fragments derived from the noncoding regions of SEQ ID NO:4 and SEQ ID NO:1 which have a length of at least 20 or 30 bases.

The sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CARD-5 probes can be used to identify tissue by species and/or by organ type.

In a similar fashion, these reagents, e.g., CARD-5 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining CARD-5 protein and/or nucleic acid expression as well as CARD-5 activity, in the context of a biological sample (e.g., blood, serum, cells, tissue) to thereby determine whether an individual is afflicted with a disease or disorder, or is at risk of developing a disorder, associated with aberrant CARD-5 expression or activity. The invention also provides for prognostic (or predictive) assays for determining whether an individual is at risk of developing a disorder associated with CARD-5 protein, nucleic acid expression or activity. For example, mutations in a CARD-5 gene can be assayed in a biological sample. Such assays can be used for prognostic or predictive purpose to thereby prophylactically treat an individual prior to the onset of a disorder characterized by or associated with CARD-5 protein, nucleic acid expression or activity.

Another aspect of the invention provides methods for determining CARD-5 protein, nucleic acid expression or CARD-5 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of CARD-5 in clinical trials.

These and other agents are described in further detail in the following sections.

1. Diagnostic Assays

An exemplary method for detecting the presence or absence of CARD-5 in a biological sample involves obtaining a biological sample from a test subject and contacting the biological sample with a compound or an agent capable of detecting CARD-5 protein or nucleic acid (e.g., mRNA, genomic DNA) that encodes CARD-5 protein such that the presence of CARD-5 is detected in the biological sample. An agent for detecting CARD-5 mRNA or genomic DNA is a labeled nucleic acid probe capable of hybridizing to CARD-5 mRNA or genomic DNA. The nucleic acid probe can be, for example, a full-length CARD-5 nucleic acid, such as the nucleic acid of SEQ ID NO:4, SEQ ID NO:6, SEQ ID NO:1 or SEQ ID NO:3, or a portion thereof, such as an oligonucleotide of at least 15, 30, 50, 100, 250 or 500 nucleotides in length and sufficient to specifically hybridize under stringent conditions to mRNA or genomic DNA. Other suitable probes for use in the diagnostic assays of the invention are described herein. An agent for detecting CARD-5 protein can be an antibody capable of binding to CARD-5 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CARD-5 mRNA, protein, or genomic DNA in a biological sample in vitro as well as in vivo. For example, in vitro techniques for detection of CARD-5 mRNA include Northern hybridizations and in situ hybridizations. In vitro techniques for detection of CARD-5 genomic DNA include Southern hybridizations. Furthermore, in vivo techniques for detection of CARD-5 protein include introducing into a subject a labeled anti-CARD-5 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. An biological sample is a peripheral blood leukocyte sample isolated by conventional means from a subject.

In another embodiment, the methods further involve obtaining a control biological sample from a control subject, contacting the control sample with a compound or agent capable of detecting CARD-5 protein, mRNA, or genomic DNA, such that the presence of CARD-5 protein, mRNA or genomic DNA is detected in the biological sample, and comparing the presence of CARD-5 protein, mRNA or genomic DNA in the control sample with the presence of CARD-5 protein, mRNA or genomic DNA in the test sample.

The invention also encompasses kits for detecting the presence of CARD-5 in a biological sample (a test sample). Such kits can be used to determine if a subject is suffering from or is at increased risk of developing a disorder associated with aberrant expression of CARD-5 (e.g., an immunological disorder). For example, the kit can comprise a labeled compound or agent capable of detecting CARD-5 protein or mRNA in a biological sample and means for determining the amount of CARD-5 in the sample (e.g., an anti-CARD-5 antibody or an oligonucleotide probe which binds to DNA encoding CARD-5, e.g., SEQ ID NO:6, SEQ ID NO:1, or SEQ ID NO:3). Kits may also include instruction for observing that the tested subject is suffering from or is at risk of developing a disorder associated with aberrant expression of CARD-5 if the amount of CARD-5 protein or mRNA is above or below a normal level.

For antibody-based kits, the kit may comprise, for example: (1) a first antibody (e.g., attached to a solid support) which binds to CARD-5 protein; and, optionally, (2) a second, different antibody which binds to CARD-5 protein or the first antibody and is conjugated to a detectable agent.

For oligonucleotide-based kits, the kit may comprise, for example: (1) a oligonucleotide, e.g., a detectably labeled oligonucleotide, which hybridizes to a CARD-5 nucleic acid sequence or (2) a pair of primers useful for amplifying a CARD-5 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of CARD-5.

2. Prognostic Assays

The methods described herein can furthermore be utilized as diagnostic or prognostic assays to identify subjects having or at risk of developing a disease or disorder associated with aberrant CARD-5 expression or activity. For example, the assays described herein, such as the preceding diagnostic assays or the following assays, can be utilized to identify a subject having or at risk of developing a disorder associated with CARD-5 protein, nucleic acid expression or activity. Alternatively, the prognostic assays can be utilized to identify a subject having or at risk for developing such a disease or disorder. Thus, the present invention provides a method in which a test sample is obtained from a subject and CARD-5 protein or nucleic acid (e.g., mRNA, genomic DNA) is detected, wherein the presence of CARD-5 protein or nucleic acid is diagnostic for a subject having or at risk of developing a disease or disorder associated with aberrant CARD-5 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CARD-5 expression or activity. For example, such methods can be used to determine whether a subject can be effectively treated with a specific agent or class of agents (e.g., agents of a type which decrease CARD-5 activity). Thus, the present invention provides methods for determining whether a subject can be effectively treated with an agent for a disorder associated with aberrant CARD-5 expression or activity in which a test sample is obtained and CARD-5 protein or nucleic acid is detected (e.g., wherein the presence of CARD-5 protein or nucleic acid is diagnostic for a subject that can be administered the agent to treat a disorder associated with aberrant CARD-5 expression or activity).

The methods of the invention can also be used to detect genetic lesions or mutations in a CARD-5 gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion characterized by at least one of an alteration affecting the integrity of a gene encoding a CARD-5-protein, or the mis-expression of the CARD-5 gene. For example, such genetic lesions can be detected by ascertaining the existence of at least one of 1) a deletion of one or more nucleotides from a CARD-5 gene; 2) an addition of one or more nucleotides to a CARD-5 gene; 3) a substitution of one or more nucleotides of a CARD-5 gene; 4) a chromosomal rearrangement of a CARD-5 gene; 5) an alteration in the level of a messenger RNA transcript of a CARD-5 gene; 6) aberrant modification of a CARD-5 gene, such as of the methylation pattern of the genomic DNA; 7) the presence of a non-wild type splicing pattern of a messenger RNA transcript of a CARD-5 gene (e.g, caused by a mutation in a splice donor or splice acceptor site); 8) a non-wild type level of a CARD-5-protein; 9) allelic loss of a CARD-5 gene; and 10) inappropriate post-translational modification of a CARD-5-protein. As described herein, there are a large number of assay techniques known in the art which can be used for detecting lesions in a CARD-5 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the CARD-3 or CARD-4-gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CARD-5 gene under conditions such that hybridization and amplification of the CARD-5-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CARD-5 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in CARD-5 can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations in CARD-5 can be identified in two-dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CARD-5 gene and detect mutations by comparing the sequence of the sample CARD-5 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the CARD-5 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type CARD-5 sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S 1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl Acad Sci USA 85:4397; Saleeba et al (1992) Methods Enzymol. 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CARD-5 cDNAs obtained from samples of cells. For example, the mutY enzyme of $E.$ $coli$ cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a CARD-5 sequence, e.g., a wild-type CARD-5 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in CARD-5 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125–144; and Hayashi (1992) Genet Anal Tech Appl 9:73–79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CARD-5 gene.

Furthermore, any cell type or tissue in which CARD-5 is expressed may be utilized in the prognostic assays described herein.

3. Pharmacogenomics

Agents, or modulators which have a stimulatory or inhibitory effect on CARD-5 activity (e.g., CARD-5 gene expression) as identified by a screening assay described herein can be administered to individuals to treat (prophylactically or therapeutically) disorders (e.g., an immunological disorder) associated with aberrant CARD-5 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of CARD-5 protein, expression of CARD-5 nucleic acid, or mutation content of CARD-5 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of CARD-5 protein or mutation content of CARD-5 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a CARD-5 modulator, such as a modulator identified by one of the exemplary screening assays described herein.

4. Monitoring of Effects During Clinical Trials

Monitoring the influence of agents (e.g., drugs, compounds) on the expression or activity of CARD-5 (e.g., the ability to modulate aberrant cell proliferation and/or differentiation) can be applied not only in basic drug screening, but also in clinical trials. For example, the effectiveness of an agent determined by a screening assay as described herein to increase CARD-5 gene expression, protein levels, or upregulate CARD-5 activity, can be monitored in clinical trails of subjects exhibiting decreased CARD-5 gene expression, protein levels, or downregulated CARD-5 activity. Alternatively, the effectiveness of an agent determined by a screening assay to decrease CARD-5 gene expression, protein levels, or downregulated CARD-5 activity, can be monitored in clinical trials of subjects exhibiting increased CARD-5 gene expression, protein levels, or upregulated CARD-5 activity. In such clinical trials, the expression or activity of CARD-5 and, preferably, other genes that have been implicated in, for example, a cellular proliferation disorder can be used as a "read out" or markers of the immune responsiveness of a particular cell.

For example, and not by way of limitation, genes, including CARD-5, that are modulated in cells by treatment with an agent (e.g., compound, drug or small molecule) which modulates CARD-5 activity (e.g., identified in a screening assay as described herein) can be identified. Thus, to study the effect of agents on cellular proliferation disorders, for example, in a clinical trial, cells can be isolated and RNA prepared and analyzed for the levels of expression of CARD-5 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CARD-5 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CARD-5 protein, mRNA, or genomic DNA in the preadministration sample; (iii) obtaining one or more post-administration samples from the subject; (iv) detecting the level of expression or activity of the CARD-5 protein, mRNA, or genomic DNA in the post-administration samples; (v) comparing the level of expression or activity of the CARD-5 protein, mRNA, or genomic DNA in the pre-administration sample with the CARD-5 protein, mRNA, or genomic DNA in the post administration sample or samples; and (vi) altering the administration of the agent to the subject accordingly. For example, increased administration of the agent may be desirable to increase the expression or activity of CARD-5 to higher levels than detected, i.e., to increase the effectiveness of the agent. Alternatively, decreased administration of the agent may be desirable to decrease expression or activity of CARD-5 to lower levels than detected, i.e., to decrease the effectiveness of the agent.

5. Transcriptional Profiling

The CARD-5 nucleic acid molecules described herein, including small oligonucleotides, can be used in transcriptionally profiling. For example, these nucleic acids can be used to examine the expression of CARD-5 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of CARD-5, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant CARD-5 expression or activity, examples of which are provided herein.

1. Prophylactic Methods

In one aspect, the invention provides a method for preventing in a subject, a disease or condition associated with an aberrant CARD-5 expression or activity, by administering to the subject an agent which modulates CARD-5 expression or at least one CARD-5 activity. Subjects at risk for a disease which is caused or contributed to by aberrant CARD-5 expression or activity can be identified by, for example, any or a combination of diagnostic or prognostic assays as described herein. Administration of a prophylactic agent can occur prior to the manifestation of symptoms characteristic of the CARD-5 aberrancy, such that a disease or disorder is prevented or, alternatively, delayed in its progression. Depending on the type of CARD-5 aberrancy, for example, a CARD-5 agonist or CARD-5 antagonist agent can be used for treating the subject. The appropriate agent can be determined based on screening assays described herein. Activities of CARD-5 that could be modulated for prophylactic purposes include, but are not limited to: 1) CARD-5 gene or protein expression, 2) CARD-5 binding to a target protein, for example, see Examples 17 for a description of proteins known to bind to CARD-5; and 3) CARD-5 regulation of NF-κB as described in Example 3.

2. Therapeutic Methods

Another aspect of the invention pertains to methods of modulating CARD-5 expression or activity for therapeutic purposes. The modulatory method of the invention involves contacting a cell with an agent that modulates one or more of the activities of CARD-5 protein activity associated with the cell. An agent that modulates CARD-5 protein activity can be an agent as described herein, such as a nucleic acid or a protein, a naturally-occurring cognate ligand of a CARD-5 protein, a peptide, a CARD-5 peptidomimetic, or other small molecule. In one embodiment, the agent stimulates one or more of the biological activities of CARD-5 protein. Examples of such stimulatory agents include active CARD-5 protein and a nucleic acid molecule encoding CARD-5 that has been introduced into the cell. In another embodiment, the agent inhibits one or more of the biological activities of CARD-5 protein. Examples of such inhibitory agents include antisense CARD-5 nucleic acid molecules and anti-CARD-5 antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a CARD-5 protein or nucleic acid molecule or a disorder related to CARD-5 expression or activity. In one embodiment, the method involves administering an agent (e.g., an agent identified by a screening assay described herein), or combination of agents that modulates (e.g., upregulates or downregulates) CARD-5 expression or activity. In another embodiment, the method involves administering a CARD-5 protein or nucleic acid molecule as therapy to compensate for reduced or aberrant CARD-5 expression or activity. Activities of CARD-5 that could be modulated for therapeutic purposes include, but are not limited to, 1) CARD-5 gene or protein expression; 2) CARD-5 binding to a target protein, for example, see Example 2 for a description of some proteins known to bind to CARD-5; 3) CARD-5 regulation of NF-κB as described in Example 3. Stimulation of CARD-5 activity is desirable in situations in which CARD-5 is abnormally downregulated and/or in which increased CARD-5 activity is likely to have a beneficial effect. Conversely, inhibition of CARD-5 activity is desirable in situations in which CARD-5 is abnormally upregulated, e.g., in myocardial infarction, and/or in which decreased CARD-5 activity is likely to have a beneficial effect. Since CARD-5 may be involved in the processing of cytokines, inhibiting the activity or expression of CARD-5 may be beneficial in patients that have aberrant inflammation.

This invention is further illustrated by the following examples that should not be construed as limiting. The contents of all references, patents and published patent applications cited throughout this application are hereby incorporated by reference.

EXAMPLES

Example 1

Isolation and Characterization of Full-Length Murine CARD-5 and Human CARD-5

The amino acid sequence of the CARD domain of RAIDD (amino acids 1 to 94) was used to search a proprietary murine cDNA sequence database using the BLASTX program with the BLOSUM62 matrix and a protein word length of three. This search led to the identification of a murine clone, jtmaa010ht2, present in a coronary artery smooth muscle cell library. This clone encodes a protein designated CARD-5. The 777 nucleotide murine CARD-5 cDNA of SEQ ID NO:1 has a 579 nucleotide open reading frame (SEQ ID NO:3) encoding a 193 amino acid protein (SEQ ID NO:2). The cDNA and protein sequences of murine CARD-5 are shown in FIG. 1.

Murine CARD-5 is predicted to be an intracellular protein having a molecular weight of 21.4 kDa prior to post-translational modification.

Figure 2:
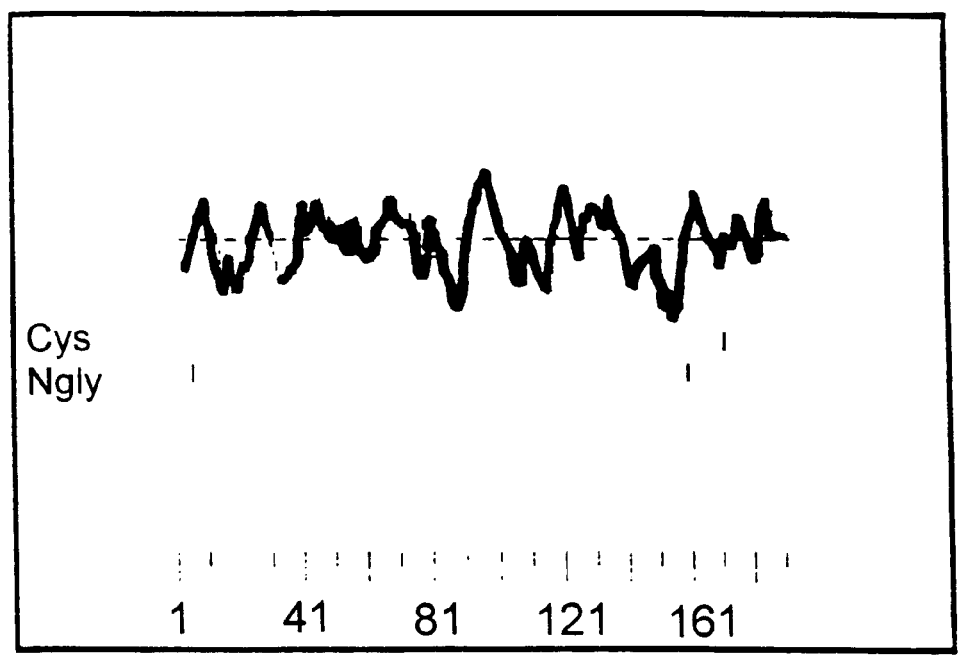
FIG. 2 depicts a hydropathy plot of murine CARD-5. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 2 depicts a hydropathy plot of murine CARD-5. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

The murine CARD-5 nucleotide sequence was used to search a proprietary database of human cDNA sequences. This search led to the identification of a human CARD-5 cDNA clone, jthza027g11t1, present in a testes library.

The 740 nucleotide human CARD-5 cDNA of SEQ ID NO:4 has a 585 nucleotide open reading frame (SEQ ID NO:6) encoding a 195 amino acid protein (SEQ ID NO:5). The cDNA and protein sequences of human CARD-5 are shown in FIG. 3.

Human CARD-5 is predicted to be an intracellular protein having a molecular weight of 21.6 kDa prior to post-translational modification.

Figure 4:
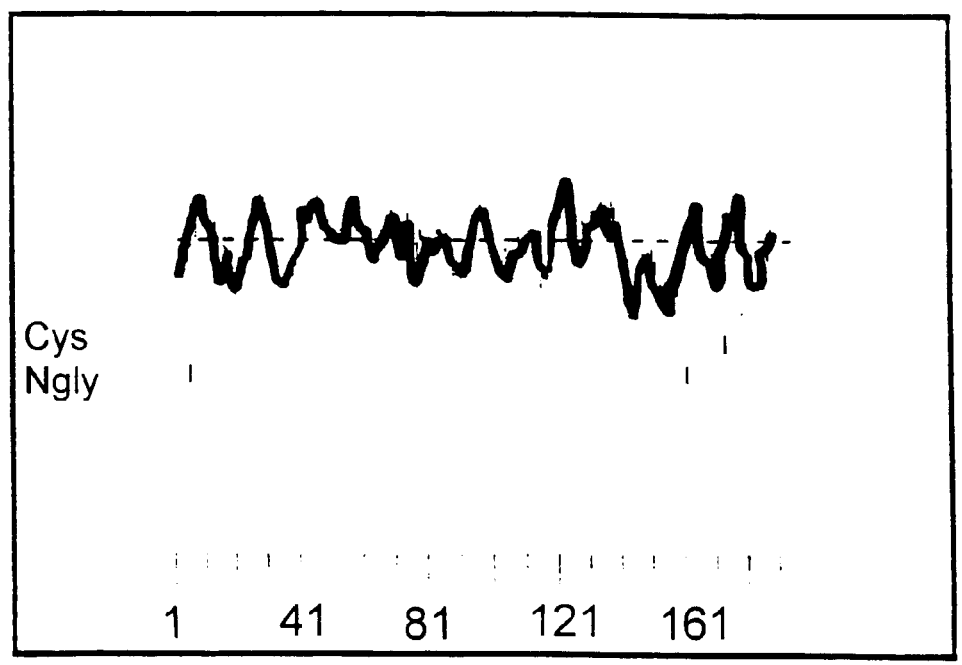
FIG. 4 depicts a hydropathy plot of human CARD-5. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 4 depicts a hydropathy plot of human CARD-5. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

FIG. 5 depicts an alignment of the cDNA sequences of murine (SEQ ID NO:1) and human (SEQ ID NO:4) CARD-5. In this alignment the sequences are 68.2% identical. FIG. 6 depicts an alignment of the amino acid sequences of murine (SEQ ID NO:2) and human (SEQ ID NO:5) CARD-5. In this alignment the sequences are 71.8% identical.

Both murine and human CARD-5 include a CARD domain. The CARD domain of murine CARD-5 extends from amino acid 110 to 193 of SEQ ID NO:2 (SEQ ID NO:7). The CARD domain of human CARD-5 extends from amino acid 111 to 195 of SEQ ID NO:5 (SEQ ID NO:8). FIG. 7 depicts an alignment of the CARD domains of murine CARD-5 (SEQ ID NO:7), human CARD-5 (SEQ ID NO:8), and RAIDD (SEQ ID NO:9).

Example 2

Identification of Interactions Between CARD-5 and Proteins with CARD Domains

A mammalian two-hybrid screening assay revealed that CARD-5 interacts with the CARD domain of several CARD domain-containing proteins.

The Stratagene® Mammalian Two-Hybrid Assay Kit (Stratagene, Inc; La Jolla, Calif.) was used to prepare a vector expressing a protein (Gal4-BD/CARD-5) consisting of the DNA binding domain of yeast Gal4 (amino acids 1–147) fused to the CARD domain of human CARD-5 (amino acids 92 to 195 of SEQ ID NO:5). For a description of the Stratagene® Mammalian Two-Hybrid Assay Kit, see, e.g., Hosfield and Chang (1999) *Strategies Newsletter* 2(2):62–65. In addition, a library of DNA sequences encoding 26 CARD domains was used to create a library of expression vectors encoding the murine NF-κB transcriptional activation domain (amino acids 364–550) fused to a CARD domain (NF-κB-AD/CARD). The Gal4-BD/CARD-5 vector, the NF-κB-AD/CARD domain vector library, and a luciferase reporter construct with an upstream Gal4 binding site were introduced into human 293T embryonic kidney cells. If a given CARD domain expressed fused to the NF-κB transcriptional activation domain interacts with the CARD domain of CARD-5, the NF-κB transcriptional activation domain will be brought into proximity with the promoter controlling luciferase expression, activating luciferase expression and permitting detection of the interaction.

The panel of CARD domains used for the mammalian two-hybrid screen included Bcl10, ARC, RICK, CARD-4, CARD-5, CARD-7, CARD-8, CARD-9, CARD-10, CARD-11, CARD-12, CARD-14, caspase-1, caspase-2, caspase-4, caspase-9, murine casepase-1, murine caspase-12, IAP-1, IAP-2, APAF1, caspase-5, caspase-13, CARD-13, CARD-6 and RAIDD.

Mammalian two-hybrid analysis revealed that the CARD domain of CARD-5 interacts with the CARD domain of caspase-1, the CARD domain of CARD-7 and with the CARD domain of CARD-5 itself.

CARD-7 contains a C-terminal CARD domain as well as an N-terminal pyrin domain, a nucleotide-binding site, and a leucine rich repeat region. CARD-7 is known to induce apoptosis through its C-terminal CARD domain. The results of the two-hybrid analysis suggest that CARD 7 is an upstream regulator or activator of CARD-5. Detailed information concerning CARD-7 can be found in U.S. application Ser. No. 09/428,252, filed Oct. 27, 1999, the content of which is incorporated herein by reference.

The C-terminal CARD domain of CARD-5 was also found to selectively bind to the CARD domain of caspase-1, suggesting that CARD-5 may be a modulator of caspase-1 activity. Caspase-1 plays a critical role in several cellular processes. For example, Caspase-1 promotes inflammation by processing an inactive cytokine precursor, e.g., the IL-1β precursor, into an active proinflammatory cytokine. Caspase-1 also plays a role in the activation of apoptosis. The caspase-1 polypeptide is initially synthesized in an inactive form that becomes activated following an oligomerization event mediated through its N-terminal CARD domain. An upstream activator of caspase-1 may possess a CARD domain that interacts with the CARD domain of caspase-1 thereby leading to its oligomerization. Furthermore, a decoy molecule that attenuates caspase-1 activation may also interact with caspase-1 via a CARD—CARD interaction. The finding that the CARD domain of CARD-5 binds selectively to the CARD domain of caspase-1 strongly suggests that CARD-5 functions as an upstream activator adaptor of caspase-1. Alternatively, CARD-5 binding to caspase-1 may attenuate the caspase-1 activation mediated by other upstream adaptors.

CARD-5 also possesses an N-terminal pyrin domain. The pyrin domain of CARD-5 extends from amino acid 1 to amino acid 88 of SEQ ID NO:2. However, additional amino acid residues may contribute to pyrin domain functionality. Thus, the domain may encompass amino acids 1–90, 1–95, or 1–100 of SEQ ID NO:2.

An upstream pyrin domain containing protein may bind to CARD-5, functioning as a regulator of CARD-5 in the context of a caspase-1 regulation pathway. For example, the upstream pyrin domain containing protein may engage the CARD-5/caspase-1 complex, e.g., via the pyrin domain of CARD-5, and thereby activate caspase-1 via its oligomerization. Examples of pyrin domain containing proteins, and possible upstream regulators of CARD-5, include NBS-1 and Pyrin-1.

Detailed information concerning NBS-1 and Pyrin-1 can be found in U.S. application Ser. No. 09/506,067, filed Feb. 17, 2000, and U.S. application Ser. No. 09/653,901, filed Sep. 1, 2000. The entire content each of these applications is incorporated herein by reference.

Detailed information concerning CARD-3, CARD-4, CARD-5, CARD-6, CARD-7, CARD-8, CARD-9, CARD-10, CARD-11, CARD-13, CARD-14, and CARD-15, can be found in U.S. application Ser. No. 09/245,281, filed Feb. 5, 1999, U.S. application Ser. No. 09/207,359, filed Dec. 8, 1998, U.S. application Ser. No. 09/099,041, filed Jun. 17, 1998, U.S. application Ser. No. 09/019,942, filed Feb. 6, 1998, U.S. application Ser. No. 09/428,252, filed Oct. 27, 1999, U.S. Application Serial No. 60/180,021, filed Feb. 3, 2000, U.S. application Ser. No. 09/573,641, filed May 17, 2000, U.S. Application Serial No. 60/181,159 filed Feb. 9, 2000, U.S. Application Serial No. 60/168,780 filed Dec. 3, 1999, U.S. application Ser. No. 09/507,533 filed Feb. 18, 2000, and U.S. application Ser. No. 09/513,904 filed Feb. 25, 2000. The entire content of each of these applications is incorporated herein by reference.

Example 3

Interaction of CARD-12 with CARD-5

Additional two-hybrid analysis revealed that the CARD domain of CARD-5 interacts with the CARD domain of CARD-12. CARD-12 contains a CARD domain, a leucine rich repeat domain, and a nucleotide binding site domain, and seven NACHT domains. Detailed information regarding CARD-12 is contained in U.S. Ser. No. 09/841,739, filed Apr. 24, 2001; U.S. Ser. No. 09/697,089 filed Oct. 26, 2000; and U.S. Serial No. 60/161,822, filed Oct. 27, 1999. The entire content of these applications is hereby incorporated by reference.

The binding of CARD-5 to CARD-12 was identified in a yeast two-hybrid assay in which the CARD domain of CARD-12 fused to the DNA binding domain of Gal4 was used to identify CARD domains that interact with the CARD domain of CARD-12.

In this analysis, the binding of the N-terminal CARD of CARD-12 to the CARD domains of 23 known proteins was assessed. The analysis involved the use of a plasmid, pCMV-CARD-12-CARD/AD, constructed by inserting the CARD domain of CARD-12 (residues 1–83) into pCMV-AD (Stratagene; La Jolla, Calif.). The panel of CARD domains used for the mammalian two-hybrid screen included Bcl10, ARC, RICK, CARD-4, CARD-5, CARD-7, CARD-8, CARD-9, CARD-10, CARD-11, CARD-12, CARD-14, CASP-1, CASP-2, CASP-4, CASP-9, mCASP1, mCASP-12, IAP-1, IAP-2, APAF1 and RAIDD. In the assay, 293T cells in 6-well plates (35-mm wells) were transfected with the following plasmids: 750 ng of pCMV-CARD-12/AD, 750 ng of pCMV-BD fused to individual CARD domains, 250 ng of pFR-Luc firefly reporter (Stratagene), and 250 ng of pRL-TK renilla reporter (Promega). Cells were harvested 24 h after transfection, and firefly luciferase activity was determined using the Dual-Luciferase Reporter Assay System (Promega). In addition, renilla luciferase activity was determined and used to normalize transfection efficiencies. The CARD of CARD-12 interacted with the CARD of CARD-5, resulting in a 10-fold increase in relative luciferase activity. CARD-12 is structurally classified as an Apaf-1/CED-4 family member, which suggests that it interacts with the downstream CARD-5 protein and induces apoptosis through the CARD-5 pyrin domain. Thus, both CARD-7 and CARD-12 are likely to be upstream regulators/activators of CARD-5.

Example 4

NF-κB Activation by CARD-5

The ability of CARD-5 modulate NF-κB activation was investigated. CARD-5 regulation of the NF-κB pathway is of interest because the NF-κB pathway is involved in many diseases described in (New England Journal of Medicine 336:1066, 1997) and (American Journal of Cardiology 76:18C, 1995) and other references known to those skilled in the art. Participation of CARD-5 in the NF-κB pathway would make CARD-5 an attractive target for drugs that modulate the NF-κB pathway for treatment of NF-κB pathway-dependent diseases, conditions, and biological processes. An NF-κB reporter plasmid was co-transfected with a construct encoding CARD-5. In the reporter plasmid, the luciferase gene was placed under the control of the NF-κB promoter. Relative luciferase activity was determined at the end of the experiment to assess NF-κB pathway activation by CARD-5. Consistent with this signal transduction model, CARD-5 was shown to be an inducer of NF-κB activation. Expression of CARD-5 in 293T cells resulted in a 20–30 fold increase in NF-κB activity.

Example 5

The Pyrin Domain of CARD-5 Mediates Apoptosis

CARD-5, which consists of an N-terminal PYRIN domain and a C-terminal CARD domain is a proapoptotic protein and is subject to methylation-induced silencing in a number of breast cancers (Conway et al. (2000) Cancer Res. 60:6236–42). This, latter observation suggests that CARD-5 may play a fundamental role in cell death. Given that CARD-12 and CARD-5 interact via their respective CARDs, the PYRIN domain of CARD-5 may function as its proapoptotic effector domain. To examine this possibility, adenovirus vectors expressing CARD-5 truncation mutants were created. Briefly, CARD-5 truncation mutants containing the PYRIN domain or the CARD domain, were cloned into the adenovirus transfer vector pLE11f, placing the gene of interest under the transcriptional control of the tetracycline-regulatable promoter. An internal ribosome entry site downstream to the gene of interest allows a modified KGFP to be expressed off the same transcript. E1/E3-deleted adenovirus was then generated by homologous recombination in 911 cells (Fallaux et al. (1996) Hum. Gene Ther. 7:215) and plaque-purified. Protein expression was verified by Western blot analysis. VERO cells were transfected (MOI=20) with recombinant adenovirus expressing full length CARD-5 (AdTRE-CARD51–195), or either of the PYRIN domain (AdTRE-CARD-5-PYR1–150) or CARD (AdTRE-CARD-5-CARD74–195) of CARD-5 alone. Thirty-six hours after transfection cells were fixed and stained with the nuclear dye Hoescht 33342 and the percentage of apoptotic versus healthy nuclei in transfected cells was then scored. Western blot for the FLAG epitope-tag indicate relative levels of expression from each vector. Thirty-six hours after transfection of VERO cells with an adenovirus expressing full length CARD-5 60.4±1.6% of cells were undergoing apoptosis. Interestingly, transfection with the PYRIN domain of CARD-5 alone resulted 66.1±5.4% of cell death. Expression of the CARD of CARD-5 alone resulted in virtually no cell death (2.6±0.6%). Similar studies carried out using rat fribroblast cells and HELA cells gave similar results. These results suggest that a PYRIN domain can play a functional role in apoptosis signaling, and substantiates the emerging hypothesis that PYRIN-containing proteins represent another important family of proteins involved in transducing the complex signals of apoptosis.

The adenovirus expression system was also used to investigate the cellular mechanisms by which CARD-5 induces cell death. Adenoviruses were constructed to express the "survival genes" p35 (a general blocker of apoptosis) and BCLxL (a blocker of cell death via mitochondrial perturbation). VERO cells were co-transfected with adenoviruses expressing: 1) complete CARD-5 or individual CARD-5 domains described above and; 2) either the p35 or BCLxL "survival genes". It was observed that p35 completely blocked CARD-5-induced cell death and CARD-5 pyrin domain-induced cell death, and that BCLxL only partially blocked CARD-5-induced cell death and CARD-5 pyrin domain-induced cell death. Further, a general caspase inhibitor (YVAD-fmk) completely blocked apoptosis when added to the medium of VERO cells infected with a CARD-5-expressing adenovirus (see Example 6). These data suggest that CARD-5 mediates apoptosis via downstream caspases rather than through a "mitochondrial pathway".

Example 6

The Role of Caspases in CARD-5-Induced Apoptosis

To investigate the role of individual classes of caspases involved with CARD-5-induced apoptosis, VERO cells were infected with the CARD-5 adenovirus (see Example 5) in the presence of various peptide-inhibitors of the caspases. The inhibitors are described in: Thorberry et al. (2000) Methods Enzymol.322:100; Talanian et al. (1997) J. Biol. Chem. 272:9677 and Thornberry et al. (1997) J. Biol. Chem. 272:17907. The various inhibitors were added to the media at a concentration of 100 μM, and the effect on CARD-5-induced apoptosis was evaluated 36 hrs after transfection with the adenovirus. CARD-5-induced apoptosis was completely blocked by a general caspase inhibitor (zVAD-fmk), as well as by an inhibitor that is relatively specific for caspase-3 (DEVD-fmk), an inhibitor that is relatively specific for caspase-4 (YVAD-fmk), an inhibitor that is relatively specific for caspase-6 (VEID-fmk), an inhibitor that is relatively specific for caspase-7 (IETD-fmk) and an inhibitor that is relatively specific for caspase-10 (AEVD-fmk). CARD-5-induced apoptosis was not blocked, or only partially blocked, by an inhibitor that is relatively specific for caspase-1 (WEHD-fmk), an inhibitor that is relatively specific for caspase-2 (VDVAD-fmk), an inhibitor that is relatively specific for caspase-9 (LEHD-fmk) and an inhibitor that is relatively specific for caspase-13 (LEED-fmk). This data is consistent with the hypothesis that CARD-5 engages downstream activators of apoptosis rather than engaging the mitochondrial apoptosis pathway.

Example 7

Deposit of Clones

A plasmid containing a cDNA encoding murine CARD-5 (EpMC5) was deposited with the American Type Culture Collection (ATCC), Manasass, Va. on Jun. 11, 1999, and assigned Accession Number PTA-212.

A clone (EpHC5) containing a cDNA molecule encoding human CARD-5, was deposited with the American Type Culture Collection (ATCC) Manassas, Va. on Jun. 11, 1999, as a composite deposit and assigned Accession Number PTA-213. To distinguish the strains and isolate a strain harboring a particular cDNA clone, one can first streak out an aliquot of the mixture to single colonies on nutrient medium (e.g., LB plates) supplemented with 100 μg/ml ampicillin, grow single colonies, and then extract the plasmid DNA from a selected colony using a standard minipreparation procedure. Next, one can digest a sample of the DNA minipreparation with a combination of the restriction enzymes Sal I and Not I and resolve the resultant products on a 0.8% agarose gel using standard DNA electrophoresis conditions. The digestion will liberate DNA fragments as follows:

Human CARD-5 (EpHC5)0.6 kb and 3.0 kb

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 19

<210> SEQ ID NO 1
<211> LENGTH: 777
<212> TYPE: DNA
<213> ORGANISM: Mus musculus
<220> FEATURE:
<221> NAME/KEY: CDS
<222> LOCATION: (89)...(667)

<400> SEQUENCE: 1

```
gtcgacccac gcgtccggca gcaggcaggc tgcagcaggc gagcagcagc aagagtaaaa        60
ggtgaccgcg gctgcccacc ccagagcc atg ggg cgg gca cga gat gcc atc          112
                                Met Gly Arg Ala Arg Asp Ala Ile
                                  1               5 ctg gac gct ctt gaa aac ttg tca ggg gat gaa ctc aaa aag ttc aag          160
Leu Asp Ala Leu Glu Asn Leu Ser Gly Asp Glu Leu Lys Lys Phe Lys
         10                  15                  20 atg aag ctg ctg aca gtg caa ctg cga gaa ggc tat ggg cgc atc cca          208
Met Lys Leu Leu Thr Val Gln Leu Arg Glu Gly Tyr Gly Arg Ile Pro
 25                  30                  35                  40 cgc ggg gcc ctg ctg cag atg gac gcc ata gat ctc act gac aaa ctt          256
Arg Gly Ala Leu Leu Gln Met Asp Ala Ile Asp Leu Thr Asp Lys Leu
                 45                  50                  55 gtc agc tac tat ctg gag tcg tat ggc ttg gag ctc aca atg act gtg          304
Val Ser Tyr Tyr Leu Glu Ser Tyr Gly Leu Glu Leu Thr Met Thr Val
             60                  65                  70 ctt aga gac atg ggc tta cag gag ctg gct gag cag ctg caa acg act          352
Leu Arg Asp Met Gly Leu Gln Glu Leu Ala Glu Gln Leu Gln Thr Thr
         75                  80                  85 aaa gaa gag tct gga gct gtg gca gct gca gcc agt gtc cct gct cag          400
Lys Glu Glu Ser Gly Ala Val Ala Ala Ala Ala Ser Val Pro Ala Gln
 90                  95                 100 agt aca gcc aga aca gga cac ttt gtg gac cag cac agg caa gca ctc          448
Ser Thr Ala Arg Thr Gly His Phe Val Asp Gln His Arg Gln Ala Leu
105                 110                 115                 120 att gcc agg gtc aca gaa gtg gac gga gtg ctg gat gct ttg cat ggc          496
Ile Ala Arg Val Thr Glu Val Asp Gly Val Leu Asp Ala Leu His Gly
                125                 130                 135 agt gtg ctg act gaa gga cag tac cag gca gtt cgt gca gag acc acc          544
Ser Val Leu Thr Glu Gly Gln Tyr Gln Ala Val Arg Ala Glu Thr Thr
            140                 145                 150 agc caa gac aag atg agg aag ctc ttc agc ttt gtt cca tcc tgg aac          592
Ser Gln Asp Lys Met Arg Lys Leu Phe Ser Phe Val Pro Ser Trp Asn
        155                 160                 165 ctg acc tgc aag gac tcc ctc ctc cag gcc ttg aag gaa ata cat ccc          640
Leu Thr Cys Lys Asp Ser Leu Leu Gln Ala Leu Lys Glu Ile His Pro
    170                 175                 180 tac ttg gtg atg gac ctg gag cag agc tgaggtatct tttccagcta              687
Tyr Leu Val Met Asp Leu Glu Gln Ser
185                 190 cattatctag ctcctgactt tgtatacaca atttttgaaa aaacaatttg tatttgtgtt       747
taaaaaaaaa aaaaaaaaaa gggcggccgc                                        777
```

<210> SEQ ID NO 2
<211> LENGTH: 193
<212> TYPE: PRT
<213> ORGANISM: Mus musculus -continued

<400> SEQUENCE: 2

```
Met Gly Arg Ala Arg Asp Ala Ile Leu Asp Ala Leu Glu Asn Leu Ser
 1               5                  10                  15

Gly Asp Glu Leu Lys Lys Phe Lys Met Lys Leu Leu Thr Val Gln Leu
            20                  25                  30

Arg Glu Gly Tyr Gly Arg Ile Pro Arg Gly Ala Leu Leu Gln Met Asp
        35                  40                  45

Ala Ile Asp Leu Thr Asp Lys Leu Val Ser Tyr Tyr Leu Glu Ser Tyr
    50                  55                  60

Gly Leu Glu Leu Thr Met Thr Val Leu Arg Asp Met Gly Leu Gln Glu
 65                  70                  75                  80

Leu Ala Glu Gln Leu Gln Thr Thr Lys Glu Glu Ser Gly Ala Val Ala
                85                  90                  95

Ala Ala Ala Ser Val Pro Ala Gln Ser Thr Ala Arg Thr Gly His Phe
            100                 105                 110

Val Asp Gln His Arg Gln Ala Leu Ile Ala Arg Val Thr Glu Val Asp
        115                 120                 125

Gly Val Leu Asp Ala Leu His Gly Ser Val Leu Thr Glu Gly Gln Tyr
    130                 135                 140

Gln Ala Val Arg Ala Glu Thr Thr Ser Gln Asp Lys Met Arg Lys Leu
145                 150                 155                 160

Phe Ser Phe Val Pro Ser Trp Asn Leu Thr Cys Lys Asp Ser Leu Leu
                165                 170                 175

Gln Ala Leu Lys Glu Ile His Pro Tyr Leu Val Met Asp Leu Glu Gln
            180                 185                 190

Ser
```

<210> SEQ ID NO 3
<211> LENGTH: 579
<212> TYPE: DNA
<213> ORGANISM: Mus musculus

<400> SEQUENCE: 3

| | |
|---|---|
| atgggcgggg cacgagatgc catcctggac gctcttgaaa acttgtcagg ggatgaactc | 60 |
| aaaaagttca agatgaagct gctgacagtg caactgcgag aaggctatgg gcgcatccca | 120 |
| cgccgggccc tgctgcagat ggacgccata gatctcactg acaaacttgt cagctactat | 180 |
| ctggagtcgt atggcttgga gctcacaatg actgtgctta gagacatggg cttacaggag | 240 |
| ctggctgagc agctgcaaac gactaaagaa gagtctggag ctgtggcagc tgcagccagt | 300 |
| gtccctgctc accaggcagt tcgtgcagag accaccagcc aagacaagat gcaagcactc | 360 |
| attgccaggg tcacagaagt ggacggagtg ctggatgctt tgcatggcag tgtgctgact | 420 |
| gaaggacagt accaggcagt tcgtgcagag accaccagcc aagacaagat gaggaagctc | 480 |
| ttcagctttg ttccatcctg gaacctgacc tgcaaggact ccctcctcca ggccttgaag | 540 |
| gaaatacatc cctacttggt gatggacctg gagcagagc | 579 |

<210> SEQ ID NO 4
<211> LENGTH: 740
<212> TYPE: DNA
<213> ORGANISM: Homo sapiens
<220> FEATURE:
<221> NAME/KEY: CDS
<222> LOCATION: (54)...(638)

<400> SEQUENCE: 4

```
cgcgtccggc tgcagcgggg tgagcggcgg cagcggccgg ggatcctgga gcc atg       56
                                                          Met
                                                            1 ggg cgc gcg cgc gac gcc atc ctg gat gcg ctg gag aac ctg acc gcc     104
Gly Arg Ala Arg Asp Ala Ile Leu Asp Ala Leu Glu Asn Leu Thr Ala
        5                  10                  15 gag gag ctc aag aag ttc aag ctg aag ctg ctg tcg gtg ccg ctg cgc     152
Glu Glu Leu Lys Lys Phe Lys Leu Lys Leu Leu Ser Val Pro Leu Arg
     20                  25                  30 gag ggc tac ggg cgc atc ccg cgg ggc gcg ctg ctg tcc atg gac gcc     200
Glu Gly Tyr Gly Arg Ile Pro Arg Gly Ala Leu Leu Ser Met Asp Ala
 35                  40                  45 ttg gac ctc acc gac aag ctg gtc agc ttc tac ctg gag acc tac ggc     248
Leu Asp Leu Thr Asp Lys Leu Val Ser Phe Tyr Leu Glu Thr Tyr Gly
 50                  55                  60                  65 gcc gag ctc acc gct aac gtg ctg cgc gac atg ggc ctg cag gag atg     296
Ala Glu Leu Thr Ala Asn Val Leu Arg Asp Met Gly Leu Gln Glu Met
             70                  75                  80 gcc ggg cag ctg cag gcg gcc acg cac cag ggc tct gga gcc gcg cca     344
Ala Gly Gln Leu Gln Ala Ala Thr His Gln Gly Ser Gly Ala Ala Pro
         85                  90                  95 gct ggg atc cag gcc cct cct cag tcg gca gcc aag cca ggc ctg cac     392
Ala Gly Ile Gln Ala Pro Pro Gln Ser Ala Ala Lys Pro Gly Leu His
     100                 105                 110 ttt ata gac cag cac cgg gct gcg ctt atc gcg agg gtc aca aac gtt     440
Phe Ile Asp Gln His Arg Ala Ala Leu Ile Ala Arg Val Thr Asn Val
 115                 120                 125 gag tgg ctg ctg gat gct ctg tac ggg aag gtc ctg acg gat gag cag     488
Glu Trp Leu Leu Asp Ala Leu Tyr Gly Lys Val Leu Thr Asp Glu Gln
130                 135                 140                 145 tac cag gca gtg cgg gcc gag ccc acc aac cca agc aag atg cgg aag     536
Tyr Gln Ala Val Arg Ala Glu Pro Thr Asn Pro Ser Lys Met Arg Lys
             150                 155                 160 ctc ttc agt ttc aca cca gcc tgg aac tgg acc tgc aag gac ttg ctc     584
Leu Phe Ser Phe Thr Pro Ala Trp Asn Trp Thr Cys Lys Asp Leu Leu
         165                 170                 175 ctc cag gcc cta agg gag tcc cag tcc tac ctg gtg gag gac ctg gag     632
Leu Gln Ala Leu Arg Glu Ser Gln Ser Tyr Leu Val Glu Asp Leu Glu
     180                 185                 190 cgg agc tgaggctcct tcccagcaac actccggtca gccctggca atcccaccaa       688
Arg Ser
 195 atcatcctga atctgatctt tttatacaca atatacgaaa agccagcttg aa            740

<210> SEQ ID NO 5
<211> LENGTH: 195
<212> TYPE: PRT
<213> ORGANISM: Homo sapiens

<400> SEQUENCE: 5

Met Gly Arg Ala Arg Asp Ala Ile Leu Asp Ala Leu Glu Asn Leu Thr
 1               5                  10                  15

Ala Glu Glu Leu Lys Lys Phe Lys Leu Lys Leu Leu Ser Val Pro Leu
             20                  25                  30

Arg Glu Gly Tyr Gly Arg Ile Pro Arg Gly Ala Leu Leu Ser Met Asp
         35                  40                  45

Ala Leu Asp Leu Thr Asp Lys Leu Val Ser Phe Tyr Leu Glu Thr Tyr
     50                  55                  60

Gly Ala Glu Leu Thr Ala Asn Val Leu Arg Asp Met Gly Leu Gln Glu
```

```
                65                  70                  75                  80
Met Ala Gly Gln Leu Gln Ala Ala Thr His Gln Gly Ser Gly Ala Ala
                    85                  90                  95

Pro Ala Gly Ile Gln Ala Pro Pro Gln Ser Ala Ala Lys Pro Gly Leu
                100                 105                 110

His Phe Ile Asp Gln His Arg Ala Ala Leu Ile Ala Arg Val Thr Asn
                115                 120                 125

Val Glu Trp Leu Leu Asp Ala Leu Tyr Gly Lys Val Leu Thr Asp Glu
    130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
                165                 170                 175

Leu Leu Gln Ala Leu Arg Glu Ser Gln Ser Tyr Leu Val Glu Asp Leu
                180                 185                 190

Glu Arg Ser
        195

<210> SEQ ID NO 6
<211> LENGTH: 585
<212> TYPE: DNA
<213> ORGANISM: Homo sapiens

<400> SEQUENCE: 6
atggggcgcg cgcgcgacgc catcctggat gcgctggaga acctgaccgc cgaggagctc      60
aagaagttca agctgaagct gctgtcggtg ccgctgcgcg agggctacgg gcgcatcccg     120
cggggcgcgc tgctgtccat ggacgccttg gacctcaccg acaagctggt cagcttctac     180
ctggagacct acggcgccga gctcaccgct aacgtgctgc gcgacatggg cctgcaggag     240
atggccgggc agctgcaggc ggccacgcac cagggctctg gagccgcgcc agctgggatc     300
caggcccctc ctcagtcggc agccaagcca ggcctgcact ttatagacca gcaccgggct     360
gcgcttatcg cgagggtcac aaacgttgag tggctgctgg atgctctgta cgggaaggtc     420
ctgacggatg agcagtacca ggcagtgcgg gccgagccca ccaacccaag caagatgcgg     480
aagctcttca gtttcacacc agcctggaac tggacctgca aggacttgct cctccaggcc     540
ctaagggagt cccagtccta cctggtggag gacctggagc ggagc                     585

<210> SEQ ID NO 7
<211> LENGTH: 84
<212> TYPE: PRT
<213> ORGANISM: Mus musculus

<400> SEQUENCE: 7

Gly His Phe Val Asp Gln His Arg Gln Ala Leu Ile Ala Arg Val Thr
1               5                   10                  15

Glu Val Asp Gly Val Leu Asp Ala Leu His Gly Ser Val Leu Thr Glu
                20                  25                  30

Gly Gln Tyr Gln Ala Val Arg Ala Glu Thr Thr Ser Gln Asp Lys Met
            35                  40                  45

Arg Lys Leu Phe Ser Phe Val Pro Ser Trp Asn Leu Thr Cys Lys Asp
        50                  55                  60

Ser Leu Leu Gln Ala Leu Lys Glu Ile His Pro Tyr Leu Val Met Asp
65                  70                  75                  80

Leu Glu Gln Ser
```

<210> SEQ ID NO 8
<211> LENGTH: 85
<212> TYPE: PRT
<213> ORGANISM: Homo sapiens

<400> SEQUENCE: 8

Gly Leu His Phe Ile Asp Gln His Arg Ala Leu Ile Ala Arg Val
1               5                   10                  15

Thr Asn Val Glu Trp Leu Leu Asp Ala Leu Tyr Gly Lys Val Leu Thr
            20                  25                  30

Asp Glu Gln Tyr Gln Ala Val Arg Ala Glu Pro Thr Asn Pro Ser Lys
        35                  40                  45

Met Arg Lys Leu Phe Ser Phe Thr Pro Ala Trp Asn Trp Thr Cys Lys
    50                  55                  60

Asp Leu Leu Gln Ala Leu Arg Glu Ser Gln Ser Tyr Leu Val Glu
65                  70                  75                  80

Asp Leu Glu Arg Ser
                85

<210> SEQ ID NO 9
<211> LENGTH: 94
<212> TYPE: PRT
<213> ORGANISM: Homo sapiens

<400> SEQUENCE: 9

Met Glu Ala Arg Asp Lys Gln Val Leu Arg Ser Leu Arg Leu Glu Leu
1               5                   10                  15

Gly Ala Glu Val Leu Val Glu Gly Leu Val Leu Gln Tyr Leu Tyr Gln
            20                  25                  30

Glu Gly Ile Leu Thr Glu Asn His Ile Gln Glu Ile Asn Ala Gln Thr
        35                  40                  45

Thr Gly Leu Arg Lys Thr Met Leu Leu Leu Asp Ile Leu Pro Ser Arg
    50                  55                  60

Gly Pro Lys Ala Phe Asp Thr Phe Leu Asp Ser Leu Gln Glu Phe Pro
65                  70                  75                  80

Trp Val Arg Glu Lys Leu Lys Lys Ala Arg Glu Glu Ala Met
                85                  90

<210> SEQ ID NO 10
<211> LENGTH: 90
<212> TYPE: PRT
<213> ORGANISM: Homo sapiens

<400> SEQUENCE: 10

Ile Ala Gln Gln Trp Ile Gln Ser Lys Arg Glu Asp Ile Val Asn Gln
1               5                   10                  15

Met Thr Glu Ala Cys Leu Asn Gln Ser Leu Asp Ala Leu Leu Ser Arg
            20                  25                  30

Asp Leu Ile Met Lys Glu Asp Tyr Glu Leu Val Ser Thr Lys Pro Thr
        35                  40                  45

Arg Thr Ser Lys Val Arg Gln Leu Leu Asp Thr Asp Ile Gln Gly
    50                  55                  60

Glu Glu Phe Ala Lys Val Ile Val Gln Lys Leu Lys Asp Asn Lys Gln
65                  70                  75                  80

Met Gly Leu Gln Pro Tyr Pro Glu Ile Leu
                85                  90

-continued

```
<210> SEQ ID NO 11
<211> LENGTH: 90
<212> TYPE: PRT
<213> ORGANISM: Homo sapiens

<400> SEQUENCE: 11

Glu Ser His Pro His Ile Gln Leu Leu Lys Ser Asn Arg Glu Leu Leu
 1               5                   10                  15

Val Thr His Ile Arg Asn Thr Gln Cys Leu Val Asp Asn Leu Leu Lys
                20                  25                  30

Asn Asp Tyr Phe Ser Ala Glu Asp Ala Glu Ile Val Cys Ala Cys Pro
            35                  40                  45

Thr Gln Pro Asp Lys Val Arg Lys Ile Leu Asp Leu Val Gln Ser Lys
        50                  55                  60

Gly Glu Glu Val Ser Glu Phe Phe Leu Tyr Leu Gln Gln Leu Ala
65                  70                  75                  80

Asp Ala Tyr Val Asp Leu Arg Pro Trp Leu
                85                  90

<210> SEQ ID NO 12
<211> LENGTH: 95
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 13, 50
<223> OTHER INFORMATION: Xaa = Any Amino Acid

<400> SEQUENCE: 12

Ala Glu Ser Gly Ser Glu Ile Ile Asp Gln His Arg Xaa Ala Leu Leu
 1               5                   10                  15

Ala Arg Val Thr Glu Asp Pro Asp Ser Leu Leu Asp Ala Leu Leu Ser
                20                  25                  30

Arg Asp Leu Ile Ser Glu Glu Asp Tyr Glu Ala Val Glu Ala Glu Thr
            35                  40                  45

Thr Xaa Leu Ser Lys Val Arg Lys Leu Leu Ile Leu Val Gln Ser Lys
        50                  55                  60

Gly Glu Glu Thr Cys Lys Phe Leu Lys Cys Leu Leu Gln Ala Leu Lys
65                  70                  75                  80

Asp Ser Ala Ala Tyr Leu Gly Leu Asp Pro Glu Val Leu Glu Ser
                85                  90                  95

<210> SEQ ID NO 13
<211> LENGTH: 97
<212> TYPE: PRT
<213> ORGANISM: Homo sapiens

<400> SEQUENCE: 13

Met Ala Thr Glu Ser Thr Pro Ser Glu Ile Ile Glu Arg Glu Arg Lys
 1               5                   10                  15

Lys Leu Leu Glu Ile Leu Gln His Asp Pro Asp Ser Ile Leu Asp Thr
                20                  25                  30

Leu Thr Ser Arg Arg Leu Ile Ser Glu Glu Tyr Glu Thr Leu Glu
            35                  40                  45

Asn Val Thr Asp Leu Leu Lys Lys Ser Arg Lys Leu Leu Ile Leu Val
        50                  55                  60

Gln Lys Lys Gly Glu Ala Thr Cys Gln His Phe Leu Lys Cys Leu Phe
65                  70                  75                  80
```

Ser Thr Phe Pro Gln Leu Ala Ala Ile Cys Gly Leu Arg His Glu Val
                85                  90                  95

Leu

<210> SEQ ID NO 14
<211> LENGTH: 108
<212> TYPE: PRT
<213> ORGANISM: Rattus norvegicus

<400> SEQUENCE: 14

Met Ala Ser Glu Gly Ala Ser Ser Glu Ile Ile Glu Lys Gln Arg Thr
 1               5                  10                  15

Lys Leu Leu Ser Val Leu Gln Gln Asp Pro Asp Ser Ile Leu Asp Thr
                20                  25                  30

Leu Thr Ser Arg Arg Leu Ile Ser Glu Glu Tyr Glu Thr Leu Glu
            35                  40                  45

Ala Ile Thr Asp Pro Leu Lys Lys Ser Arg Lys Leu Leu Ile Leu Ile
        50                  55                  60

Gln Lys Lys Gly Glu Asp Ser Cys Cys Cys Phe Leu Lys Cys Leu Ser
65                  70                  75                  80

Asn Ala Phe Pro Gln Ser Ala Ser Thr Leu Gly Leu Lys Gln Glu Val
                85                  90                  95

Pro Arg Gln Gly Thr Gly Glu Val Val Glu Val Ser
            100                 105

<210> SEQ ID NO 15
<211> LENGTH: 85
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2, 5, 18, 20, 21, 29, 34, 45-47, 56, 61, 67, 72, 74-75,
      84
<223> OTHER INFORMATION: Xaa = Any Amino Acid

<400> SEQUENCE: 15

Gly Xaa His Phe Xaa Asp Gln His Arg Ala Ala Leu Ile Ala Arg Val
 1               5                  10                  15

Thr Xaa Val Xaa Xaa Val Leu Asp Ala Leu Tyr Gly Xaa Val Leu Thr
                20                  25                  30

Glu Xaa Gln Tyr Gln Ala Val Arg Ala Glu Thr Thr Xaa Xaa Xaa Lys
            35                  40                  45

Met Arg Lys Leu Phe Ser Phe Xaa Pro Ser Trp Asn Xaa Thr Cys Lys
        50                  55                  60

Asp Xaa Leu Leu Gln Ala Leu Xaa Glu Xaa Xaa Pro Tyr Leu Val Glu
65                  70                  75                  80

Asp Leu Glu Xaa Ser
                85

<210> SEQ ID NO 16
<211> LENGTH: 25
<212> TYPE: DNA
<213> ORGANISM: Homo sapiens

<400> SEQUENCE: 16
taggacctcg gtaccgcgc gcgcg                                          25

<210> SEQ ID NO 17
<211> LENGTH: 25
<212> TYPE: DNA
<213> ORGANISM: Homo sapiens

<400> SEQUENCE: 17
cgccggcccc taggacctcg gtacc                                          25

<210> SEQ ID NO 18
<211> LENGTH: 777
<212> TYPE: DNA
<213> ORGANISM: Mus musculus

<400> SEQUENCE: 18

| gcggccgccc | tttttttttt | tttttttta  | aacacaaata | caaattgttt | tttcaaaaat |  60 |
| tgtgtataca | aagtcaggag | ctagataatg | tagctggaaa | agatacctca | gctctgctcc | 120 |
| aggtccatca | ccaagtaggg | atgtatttcc | ttcaaggcct | ggaggaggga | gtccttgcag | 180 |
| gtcaggttcc | aggatggaac | aaagctgaag | agcttcctca | tcttgtcttg | gctggtggtc | 240 |
| tctgcacgaa | ctgcctggta | ctgtccttca | gtcagcacac | tgccatgcaa | agcatccagc | 300 |
| actccgtcca | cttctgtgac | cctggcaatg | agtgcttgcc | tgtgctggtc | cacaaagtgt | 360 |
| cctgttctgg | ctgtactctg | agcagggaca | ctggctgcag | ctgccacagc | tccagactct | 420 |
| tctttagtcg | tttgcagctg | ctcagccagc | tcctgtaagc | ccatgtctct | aagcacagtc | 480 |
| attgtgagct | ccaagccata | cgactccaga | tagtagctga | caagtttgtc | agtgagatct | 540 |
| atggcgtcca | tctgcagcag | ggccccgcgt | gggatgcgcc | catagccttc | tcgcagttgc | 600 |
| actgtcagca | gcttcatctt | gaactttttg | agttcatccc | ctgacaagtt | ttcaagagcg | 660 |
| tccaggatgg | catctcgtgc | ccgccccatg | gctctgggt  | gggcagccgc | ggtcaccttt | 720 |
| tactcttgct | gctgctcgcc | tgctgcagcc | tgcctgctgc | cggacgcgtg | ggtcgac    | 777 |

<210> SEQ ID NO 19
<211> LENGTH: 740
<212> TYPE: DNA
<213> ORGANISM: Homo sapiens

<400> SEQUENCE: 19

| ttcaagctgg | cttttcgtat | attgtgtata | aaaagatcag | attcaggatg | atttggtggg |  60 |
| attgccaggg | gctgaccgga | gtgttgctgg | gaaggagcct | cagctccgct | ccaggtcctc | 120 |
| caccaggtag | gactgggact | cccttagggc | ctggaggagc | aagtccttgc | aggtccagtt | 180 |
| ccaggctggt | gtgaaactga | agagcttccg | catcttgctt | gggttggtgg | gctcggcccg | 240 |
| cactgcctgg | tactgctcat | ccgtcaggac | cttcccgtac | agagcatcca | gcagccactc | 300 |
| aacgtttgtg | accctcgcga | taagcgcagc | ccggtgctgg | tctataaagt | gcaggcctgg | 360 |
| cttggctgcc | gactgaggag | gggcctggat | cccagctggc | gcggctccag | agccctggtg | 420 |
| cgtggccgcc | tgcagctgcc | cggccatctc | ctgcaggccc | atgtcgcgca | gcacgttagc | 480 |
| ggtgagctcg | gcgccgtagg | tctccaggta | gaagctgacc | agcttgtcgg | tgaggtccaa | 540 |
| ggcgtccatg | gacagcagcg | cgccccgcgg | gatgcgcccg | tagccctcgc | gcagcggcac | 600 |
| cgacagcagc | ttcagcttga | acttcttgag | ctcctcggcg | gtcaggttct | ccagcgcatc | 660 |
| caggatggcg | tcgcgcgcgc | gccccatggc | tccaggatcc | ccggccgctg | ccgccgctca | 720 |
| ccccgctgca | gccggacgcg |            |            |            |            | 740 |

What is claimed is:

1. A method for identifying a compound which binds to CARD-5, the method comprising:
   a) contacting a polypeptide, comprising amino acids 1–88 or 111–195 of SEQ ID NO:5 with a test compound; and
   b) determining whether the test compound binds to the polypeptide.

2. A method for identifying a compound that modulates an activity of CARD-5, comprising:
   a) contacting a polypeptide comprising amino acids 1–88 or 111–195 of SEQ ID NO:5 with a test compound; and
   b) determining the effect of the test compound on an activity of the polypeptide, to thereby identify a compound which modulates the activity of the polypeptide.

3. The method of claim 1, wherein the polypeptide comprises amino acids 1–88 of SEQ ID NO:5.

4. The method of claim 3, wherein the polypeptide is a fusion protein.

5. The method of claim 3, wherein the polypeptide is an isolated polypeptide.

6. The method of claim 3, wherein the test compound is a peptide, peptidomimetic, or small molecule.

7. The method of claim 3, wherein the binding of the test compound to the polypeptide is determined by direct detecting of test compound/polypeptide binding.

8. The method of claim 3, wherein the binding of the test compound to the polypeptide is determined by detection of binding using a competition binding assay.

9. The method of claim 1, wherein the polypeptide comprises amino acids 111–195 of SEQ ID NO:5.

10. The method of claim 9, wherein the polypeptide is a fusion protein.

11. The method of claim 9, wherein the polypeptide is an isolated polypeptide.

12. The method of claim 9, wherein the test compound is a peptide, peptidomimetic, or small molecule.

13. The method of claim 9, wherein the binding of the test compound to the polypeptide is determined by direct detecting of test compound polypeptide binding.

14. The method of claim 9, wherein the binding of the test compound to the polypeptide is determined by detection of binding using a competition binding assay.

15. The method of claim 1, wherein the polypeptide comprises SEQ ID NO:5.

16. The method of claim 15, wherein the polypeptide is a fusion protein.

17. The method of claim 15, wherein the polypeptide is an isolated polypeptide.

18. The method of claim 15, wherein the test compound is a peptide, peptidomimetic, or small molecule.

19. The method of claim 15, wherein the binding of the test compound to the polypeptide is determined by direct detecting of test compound-polypeptide binding.

20. The method of claim 15, wherein the binding of the test compound to the polypeptide is determined by detection of binding using a competition binding assay.

21. The method of claim 2, wherein the polypeptide comprises amino acids 111–195 of SEQ ID NO:5.

22. The method of claim 21, wherein the polypeptide is a fusion protein.

23. The method of claim 21, wherein the test compound is a peptide, peptidomimetic, or small molecule.

24. The method of claim 2, wherein the polypeptide comprises amino acids 1–88 of SEQ ID NO:5.

25. The method of claim 24, wherein the polypeptide is a fusion protein.

26. The method of claim 24, wherein the test compound is a peptide, peptidomimetic, or small molecule.

27. The method of claim 24, wherein the activity is induction of apoptosis.

28. The method of claim 2, wherein the polypeptide comprises SEQ ID NO:5.

29. The method of claim 28, wherein the polypeptide is a fusion protein.

30. The method of wherein the test compound is a peptide, peptidomimetic, or small molecule.

31. The method of claim 28, wherein the activity is induction of apoptosis.

32. The method of claim 28, wherein the activity is activation of NF-kB.

33. A method of identifying a compound that reduces or blocks the binding of CARD-5 to a CARD-5 ligand, the method comprising:
   contacting, in the presence of a test compound, a first polypeptide comprising amino acids 111–195 of SEQ ID NO:5 with a second polypeptide comprising the CARD of caspase-1, CARD-7, CARD-12, or CARD-5;
   measuring the binding of the first polypeptide to the second polypeptide; and
   comparing the measured binding of the first polypeptide to the second polypeptide with the binding of the first polypeptide to the second polypeptide in the absence of the test compound, to thereby determine whether the test compound reduces or blocks the binding of CARD-5 to a CARD-5 ligand.

34. The method of claim 33, wherein the first polypeptide is a fusion protein.

35. The method of claim 33, wherein the first and second polypeptides are isolated polypeptides.

36. The method of claim 33, wherein the test compound is a peptide, peptidomimetic, or small molecule.

37. The method of claim 33, wherein the second polypeptide comprises the CARD of caspase-1.

38. The method of claim 33, wherein the second polypeptide comprises the CARD of CARD-7.

39. The method of claim 33, wherein the second polypeptide comprises the CARD of CARD-12.

40. The method of claim 33, wherein the second polypeptide comprises the CARD of CARD-5.

41. The method of claim 33, wherein the first polypeptide comprises SEQ ID NO:5.

42. The method of claim 41, wherein the first polypeptide is a fusion protein.

43. The method of claim 41, wherein the first and second polypeptides are isolated polypeptides.

44. The method of claim 41, wherein the test compound is a peptide, peptidomimetic, or small molecule.

45. The method of claim wherein the second polypeptide comprises the CARD of caspase-1.

46. The method of claim 41, wherein the second polypeptide comprises the CARD of CARD-7.

47. The method of claim 41, wherein the second polypeptide comprises the CARD of CARD-12.

48. The method of claim wherein the second polypeptide comprises the CARD of CARD-5.

* * * * *